(12) United States Patent
Boudreaux

(10) Patent No.: US 10,856,931 B2
(45) Date of Patent: Dec. 8, 2020

(54) COMPOUND SCREW KNIFE DRIVE FOR ELECTROSURGICAL SHEARS

(71) Applicant: ETHICON LLC, Guaynabo, PR (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 372 days.

(21) Appl. No.: 15/989,442

(22) Filed: May 25, 2018

(65) Prior Publication Data

US 2019/0357965 A1    Nov. 28, 2019

(51) Int. Cl.
*A61B 18/14*    (2006.01)
*A61B 18/12*    (2006.01)
*A61B 18/00*    (2006.01)

(52) U.S. Cl.
CPC ...... *A61B 18/1442* (2013.01); *A61B 18/1206* (2013.01); *A61B 2018/0063* (2013.01);
(Continued)

(58) Field of Classification Search
CPC ............ A61B 18/1206; A61B 18/1442; A61B 2018/00601; A61B 2018/0063; A61B 2018/126; A61B 2018/1455
See application file for complete search history.

(56) References Cited

U.S. PATENT DOCUMENTS 6,500,176 B1    12/2002 Truckai et al.
7,112,201 B2    9/2006 Truckai et al.
(Continued)

OTHER PUBLICATIONS

U.S. Appl. No. 15/989,424, entitled "Method and Apparatus for Open Electrosurgical Shears," filed May 25, 2018.
(Continued)

*Primary Examiner* — Michael F Peffley
(74) *Attorney, Agent, or Firm* — Frost Brown Todd LLC

(57) ABSTRACT

A surgical instrument includes an end effector, a handle assembly, and a knife drive assembly. The end effector includes a first jaw, a second jaw, a knife, and an electrode assembly. The second jaw is pivotably coupled with the first jaw and is operable to move between an open position and a closed position. The knife is configured to actuate between a pre-fired position and a fired position. The electrode assembly is configured to apply RF energy to tissue. The handle assembly includes a housing associated with the first jaw and an arm associated with the second jaw. The arm is configured to pivot the second jaw between the open position and the closed position. The knife drive assembly includes an input assembly, an output assembly, and a threaded member rotatably disposed within the housing. The threaded member includes a first threaded portion and a second threaded portion. The first threaded portion is associated with the input assembly and includes a first pitch extending in a first pitch orientation. The second threaded portion is associated with the output assembly and includes a second pitch extending in a second pitch orientation. The second pitch orientation is opposite the first pitch orientation. The input assembly is capable to travel a first proximal distance in order to rotate the threaded member. The threaded member is capable to rotate to drive the output assembly a first distal distance to actuate the knife from the pre-fired position to the fired position.

20 Claims, 22 Drawing Sheets

(52) U.S. Cl.
CPC .............. *A61B 2018/00601* (2013.01); *A61B 2018/126* (2013.01); *A61B 2018/1455* (2013.01)

(56) References Cited

U.S. PATENT DOCUMENTS

| | | | |
|---|---|---|---|
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 8,936,595 | B2 * | 1/2015 | Mitzlaff ............. A61B 18/1442 606/51 |
| 8,939,974 | B2 | 1/2015 | Boudreaux et al. |
| 9,089,327 | B2 | 7/2015 | Worrell et al. |
| 9,101,385 | B2 * | 8/2015 | Shelton, IV ....... A61B 18/1445 |
| 9,161,803 | B2 | 10/2015 | Yates et al. |
| 9,402,682 | B2 | 8/2016 | Worrell et al. |
| 9,545,253 | B2 | 1/2017 | Worrell et al. |
| 9,610,114 | B2 | 4/2017 | Baxter, III et al. |
| 9,877,720 | B2 | 1/2018 | Worrell et al. |
| 2009/0149854 | A1 * | 6/2009 | Cunningham ..... A61B 18/1442 606/51 |
| 2014/0246473 | A1 * | 9/2014 | Auld ...................... A61B 90/98 227/175.1 |
| 2016/0175031 | A1 * | 6/2016 | Boudreaux ........ A61B 18/1442 606/52 |
| 2017/0128120 | A1 * | 5/2017 | Cho .................... A61B 18/1442 |
| 2017/0172594 | A1 * | 6/2017 | Allen, IV ............. A61B 17/295 |

OTHER PUBLICATIONS

U.S. Appl. No. 15/989,430, entitled "Electrosurgical Shears with Knife Lock and Clamp-Actuated Switch," filed May 25, 2018.

U.S. Appl. No. 15/989,433, entitled "Knife Drive Assembly for Electrosurgical Shears," filed May 25, 2018.

U.S. Appl. No. 15/989,438, entitled "Knife Auto-Return Assembly for Electrosurgical Shears," filed May 25, 2018.

U.S. Appl. No. 15/989,448, entitled "Firing and Lockout Assembly for Knife for Electrosurgical Shears," filed May 25, 2018.

U.S. Appl. No. 15/989,452, entitled "Dual Stage Energy Activation for Electrosurgical Shears," filed May 25, 2018.

U.S. Appl. No. 15/989,455, entitled "Latching Clamp Arm for Electrosurgical Shears," filed May 25, 2018.

* cited by examiner

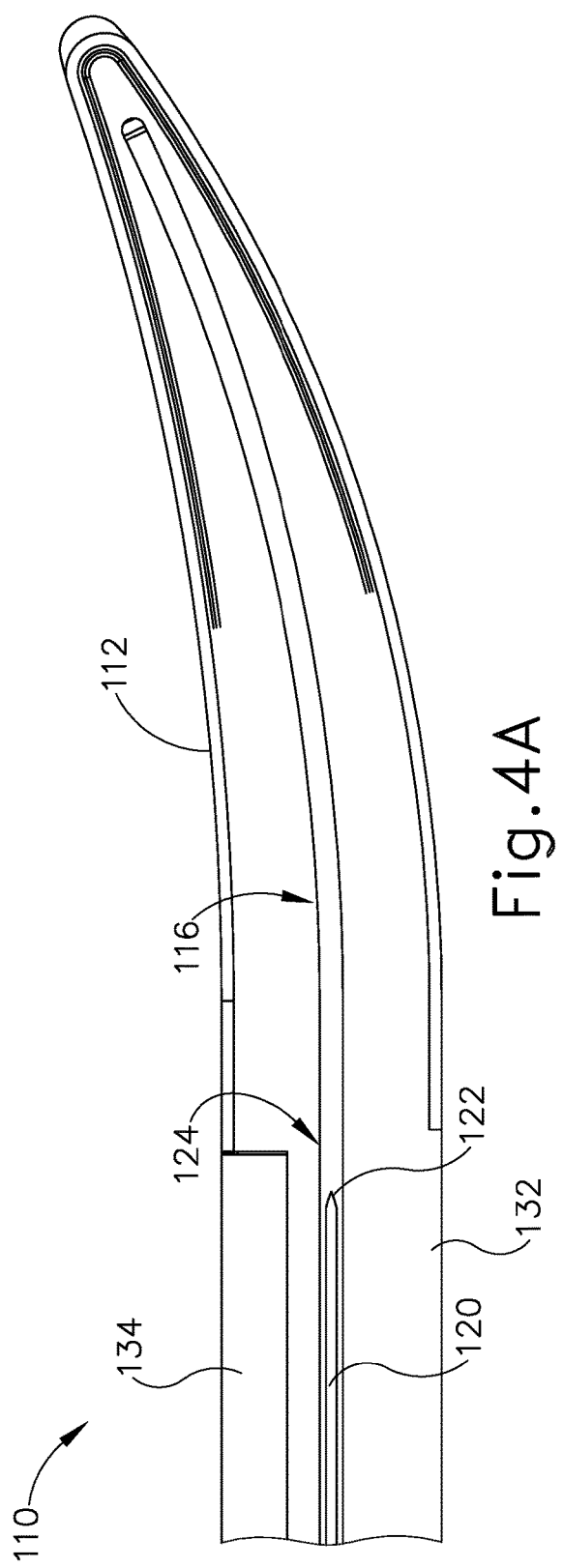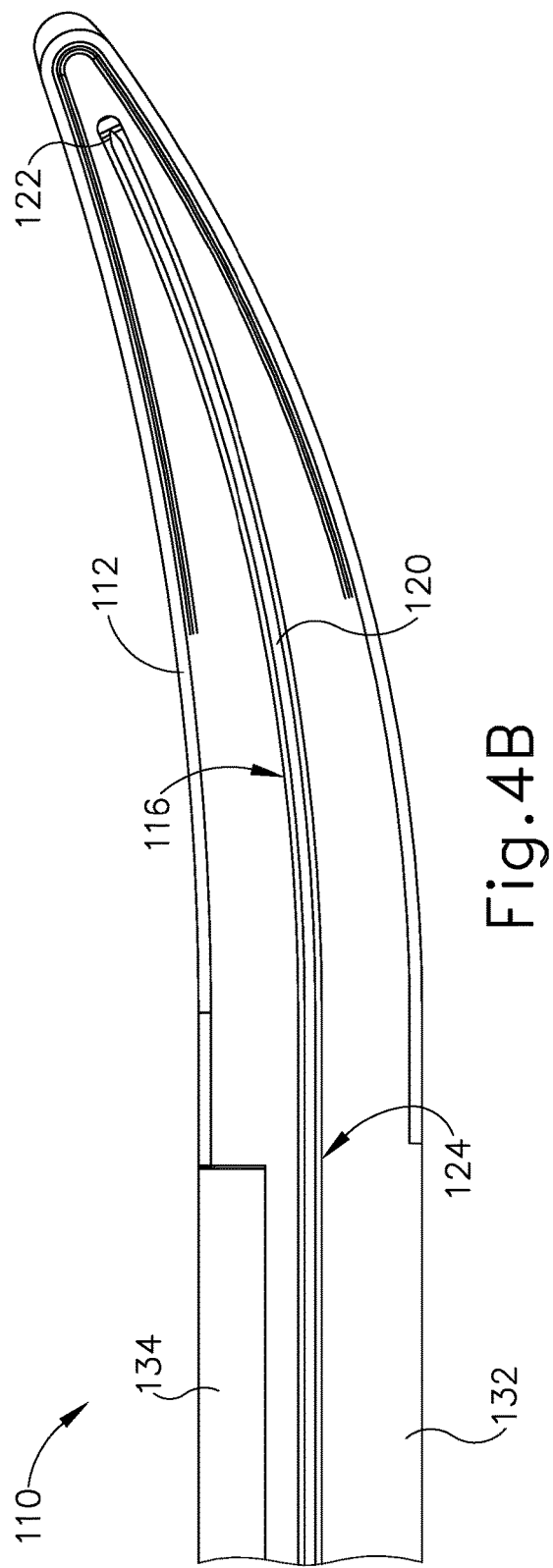

COMPOUND SCREW KNIFE DRIVE FOR ELECTROSURGICAL SHEARS

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL.® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein.

Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue. When an instrument includes grasping jaws and tissue severing capabilities, the instrument may also include a feature that ensures full closure of the jaws before the tissue is severed and/or before the electrodes are activated.

While various kinds of surgical instrument have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional view of the end effector of FIG. 1, taken along line 4-4 of FIG. 1, where the translating knife of FIG. 2 is in the proximal position;

FIG. 4B depicts a cross-sectional view of the end effector of FIG. 1, taken along line 4-4 of FIG. 1, where the translating knife of FIG. 2 is in the distal position;

Figure 1:
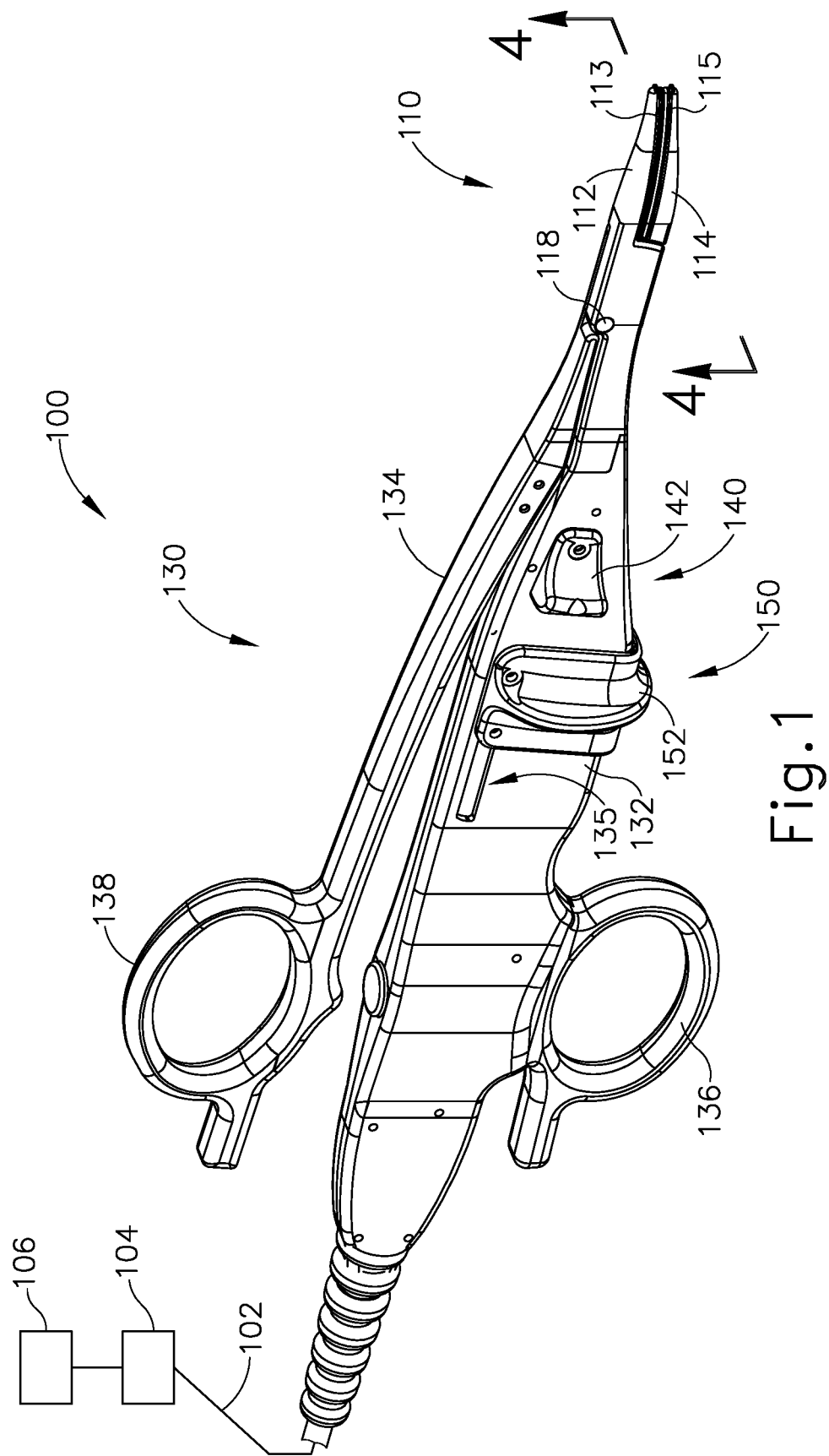
FIG. 1 depicts a perspective view of an exemplary electrosurgical forceps instrument, where an end effector is in a closed position, where a resilient arm is in a relaxed position.
Figure 2:
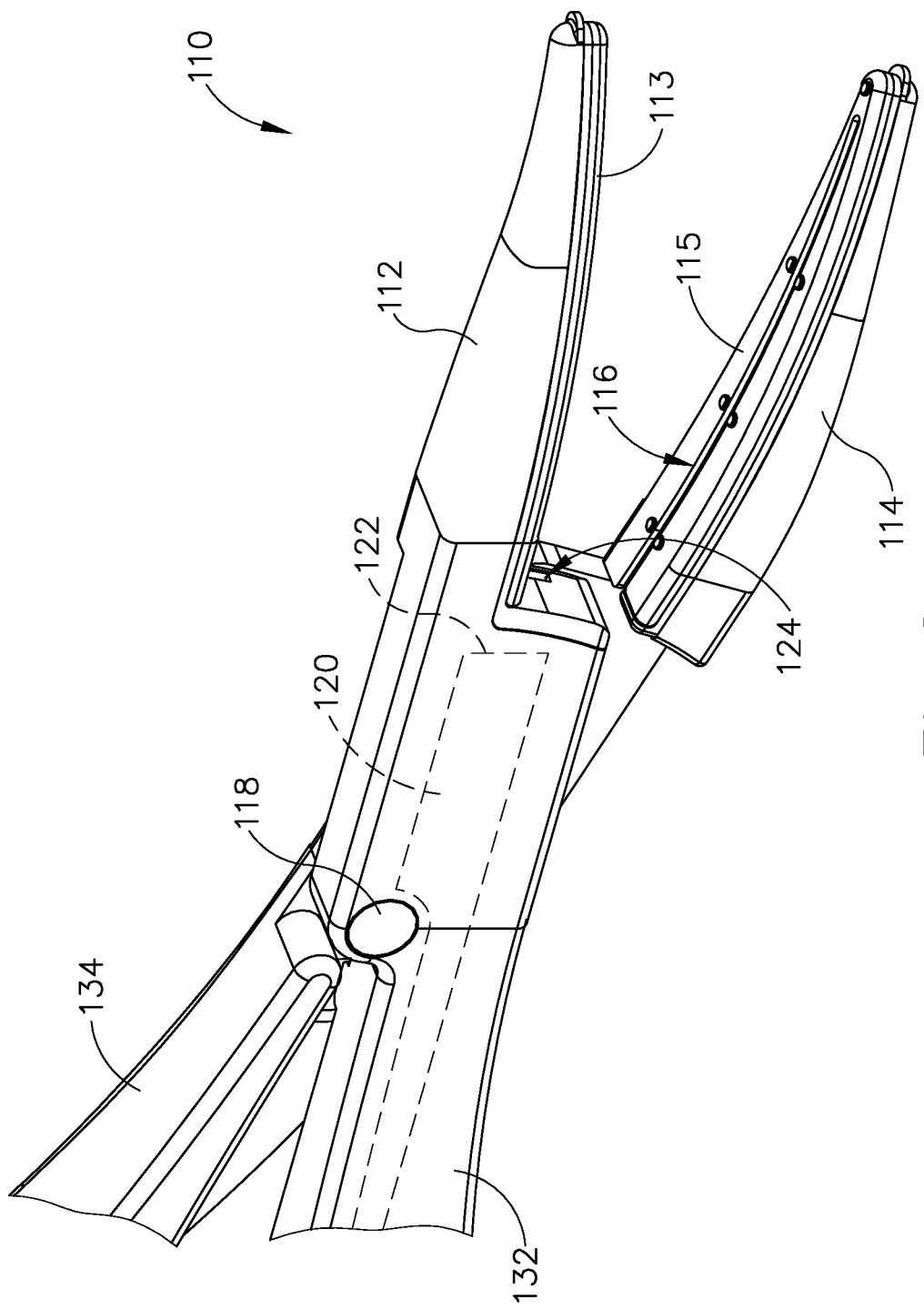
FIG. 2 depicts a perspective view of the end effector of FIG. 1 in an opened position, where a translating knife is in a proximal position.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Electrosurgical Forceps

As previously noted, an electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated before or after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handle assembly may be positioned at the proximal end of the shaft for manipulating the end effector. Such a handle assembly may have a pistol grip configuration or some other configuration.

In some instances, it may be desirable to provide an electrosurgical instrument that does not have an elongate shaft or handle assembly similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pat. No. 9,610,144, entitled "Electrosurgical Hand Shears," filed Jan. 29, 2013, the disclosure of which is incorporated by reference herein. Various other examples of electrosurgical forceps instruments will be described in greater detail below; while other examples will be apparent to those of ordinary skill in the art in view of the teachings herein.

FIGS. 1-4B show an exemplary electrosurgical forceps instrument (100). Instrument (100) includes a handle assembly (130) extending distally into an end effector (110). As will be described in greater detail below, instrument (100) may be used to grasp, seal, and sever tissue captured by end effector (110).

End effector (110) includes a first jaw (112) having a first electrode (113), a second jaw (114) having a second electrode (115), and a knife (120) configured to translate through the first jaw (112) and the second jaw (114). First jaw (112)

and second jaw (114) are pivotably coupled with each other via pivot pin (118). First jaw (112) and second jaw (114) may pivot between an open position (FIG. 2) and a closed position (FIG. 1) in order to grasp tissue. First and second electrodes (113, 115) are positioned on respective jaws (112, 114) such that electrodes (113, 115) face each other when jaws (112, 114) are pivoted into the closed position. Additionally, each electrode (113, 115) is U-shaped in the present example, with the bend of the U-shape located near the distal end of each respective jaw (112, 114), such that each electrode (113, 115) includes two longitudinally extending, laterally spaced-apart legs extending along the length of each respective jaw (112, 114). Laterally spaced-apart legs of each electrode (113, 115) and corresponding portions of jaws (112, 114) define an elongate slot (116). Elongate slot (116) is dimensioned to slidably receive knife (120) such that knife may translate from a proximal position (FIG. 4A) to a distal position (FIG. 4B). Knife (120) includes a distal cutting edge (122) configured to sever tissue captured between jaws (112, 114) in the closed position.

A cable (102) extends proximally from handle assembly (130). Cable (102) is coupled with a control unit (104), which is further coupled with a power source (106). Power source (106) may power control unit (104). Control unit (104) is operable to provide RF power to electrodes (113, 115) of jaws (112, 114), to thereby seal tissue suitably captured between jaws (112, 114).

Handle assembly (130) includes a housing (132), and a resilient arm (134). Housing (132) contains an electrode activation assembly (140) and a firing assembly (150). Housing (132) and resilient arm (134) are pivotably coupled with each other via pivot pin (118). Housing (132) extends distally into first jaw (112), while resilient arm (134) extends distally into second jaw (114). Housing (132) defines a knife pathway (124) that slidably houses knife (120). Housing (132) includes a finger ring (136) while resilient arm (134) terminates proximally into a thumb ring (138). Therefore, the operator may grasp instrument (100) in a scissor grip fashion and pivot resilient arm (134) relative to housing (132) via rings (136, 138) in order to open and close jaws (112, 114).

Resilient arm (134) is sufficiently resilient that arm (134) may flex from a relaxed position (FIG. 3B) to a flexed position (FIG. 3C) in response to pivoting arm (134) further toward housing (132) when jaws (112, 114) are already in the closed position. Resilient arm (134) is biased toward the relaxed position. Further pivoting of resilient arm (134) into the flexed position may result in greater closure forces between jaws (112, 114) as compared to pivoting jaws (112, 114) into the closed position while arm (134) is in the relaxed position. Resilient arm (134) may be suitably resilient such that when resilient arm (134) is pivoted into the flexed position, the closure force between jaws (112, 114) is sufficient such that electrodes (113, 115) may properly seal tissue grasped between jaws (112, 114). Additionally, the resilient nature of arm may limit the amount of closure force between jaws (112, 114) such that jaws (112, 114) may not compress tissue too much, resulting in inadvertent tissue damage. When the operator no longer desires to compress tissue between jaws (112, 114) to properly seal clamped tissue, the operator may reduce the amount of closure force applied to resilient arm (134) such that arm (134) returns to the relaxed state.

Housing (132) slidingly supports an RF trigger (142) of electrode activation assembly (140). RF trigger (142) is in communication with control unit (104). RF trigger (142) may be pressed or actuated to command control unit (104) to supply RF energy to electrodes (113, 115) of end effector (110). RF trigger (142) may electrically couple with control unit (104) through any suitable components known to a person having ordinary skill in the art in view of the teachings herein.

As will be described in greater detail below, firing assembly (150) is configured to actuate knife (120) within jaws (112, 114) from a proximal position to a distal position in order to sever tissue captured between jaws (112, 114). Previous firing assemblies for electrosurgical forceps may have had a trigger that was a lever arm configured to rotate relative to a handle assembly to actuate a knife. The lever arm may have extended away from the handle assembly in order to provide a mechanical advantage for actuating knife within jaws (112, 114). However, when lever arm extends away from handle assembly, it may become difficult rotate lever arm when instrument is flipped such that thumb ring becomes finger rings and vice versa. In such instances when instrument is flipped, the lever arm may no longer associate with the index/middle finger for actuating the lever arm.

Therefore, it may be desirable to have a compact firing assembly with a trigger close to the center of housing such that it is easy to actuate firing assembly with the same finger(s), even when instrument is flipped. Firing assembly (150) of the current example includes a knife trigger (152) slidably coupled with housing (132) via a slot (135). Trigger (152) is close to the center of housing (132) such that trigger (152) may be easily accessed regardless if instrument (100) is flipped around. Trigger (152) may actuate relative to housing (132) in order to actuate a knife (120) of end effector (110). In particular, proximal translation of trigger (152) results in distal translation of knife (120), while distal translation of trigger (152) results in proximal translation of knife (120). Trigger (152) may be biased toward the distal position such that knife (120) is biased toward the proximal position.

Trigger (152) may be coupled with knife (120) through any suitably firing mechanism assembly as would be apparent to one having ordinary skill in the art in view of the teachings herein. It should be understood that trigger (152) may be selectively actuated at any suitable time the operator desires. For instance, the operator may grasp tissue by pivoting jaws (112, 114) to the closed position, wait a desired amount of time, and fire trigger (152) to actuate knife (120) and sever tissue. Alternatively, the operator may grasp tissue by pivoting jaws (112, 114), release tissue if jaws (112, 114) are not satisfactorily grasping tissue, re-grasp tissue, and then fire trigger (152) to actuate knife (120) and sever tissue.

Figure 3A:
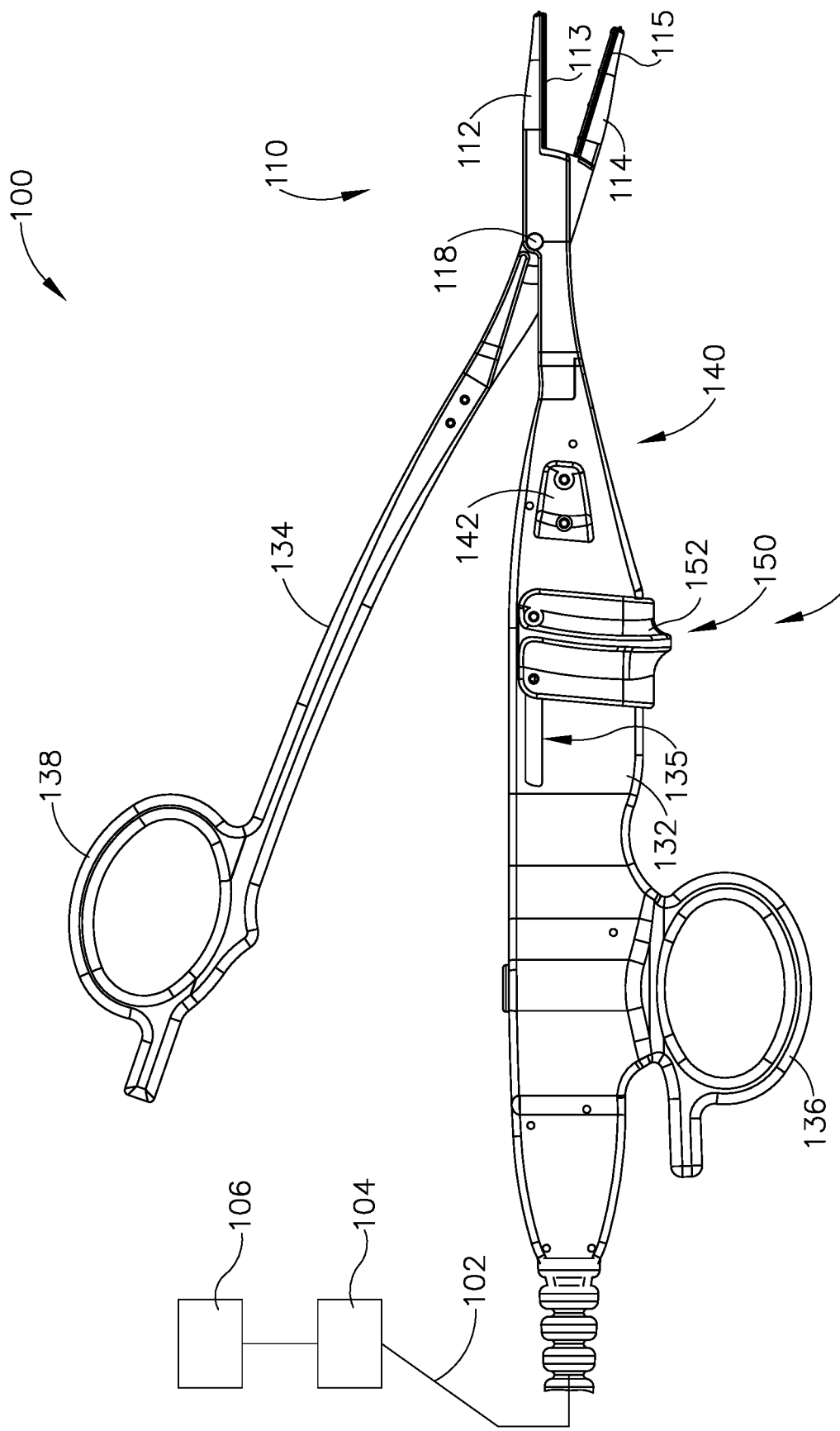
FIG. 3A depicts a side elevational view of the electrosurgical forceps instrument of FIG. 1, where the end effector is in the opened position, where the resilient arm is in the relaxed position, and where the translating knife of FIG. 2 is in the proximal position.
Figure 3B:
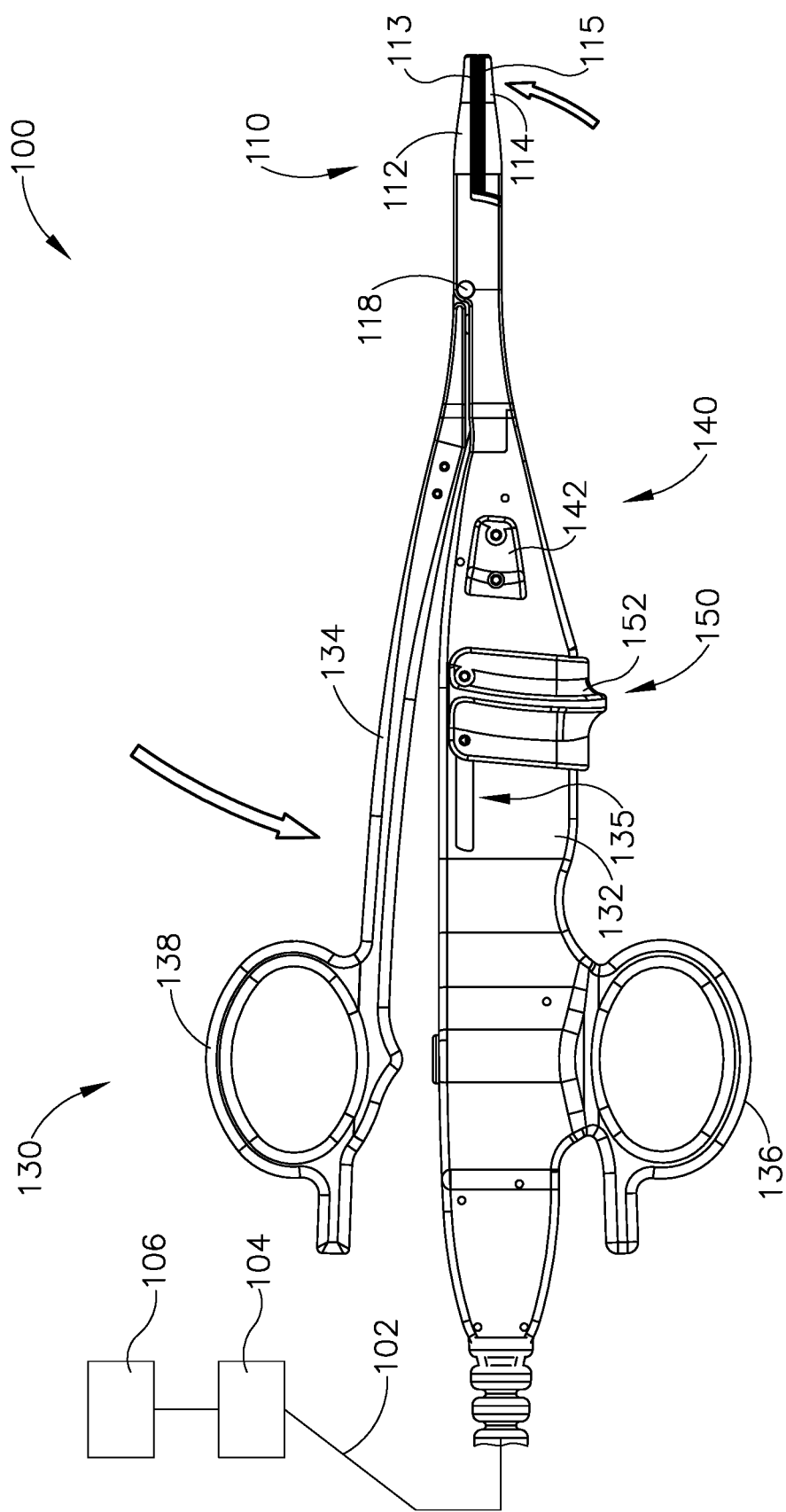
FIG. 3B depicts a side elevational view of the electrosurgical forceps instrument of FIG. 1, where the end effector is in the closed position, where the resilient arm is in the relaxed position, and where the translating knife of FIG. 2 is in the proximal position.

FIGS. 3A-4B show an exemplary operation of instrument (100). FIG. 3A shows jaws (112, 114) of end effector (110) in the opened position. Therefore, resilient arm (134) is pivoted away from housing (132). As shown in FIG. 3B, when the operator desires to initially grasp and manipulate tissue, the operator may pivot resilient arm (134) toward housing (132) such that jaws (112, 114) are pivoted toward the closed position while resilient arm (134) remains in the relaxed position. With jaws (112, 114) pivoted toward the closed position, the operator may manipulate tissue grasped by jaws (112, 114). It should be understood that the closure forces imparted on tissue by jaws (112, 114) at this point may not be sufficient enough for suitable sealing of tissue via RF energy provided by electrodes (113, 115).

Figure 3C:
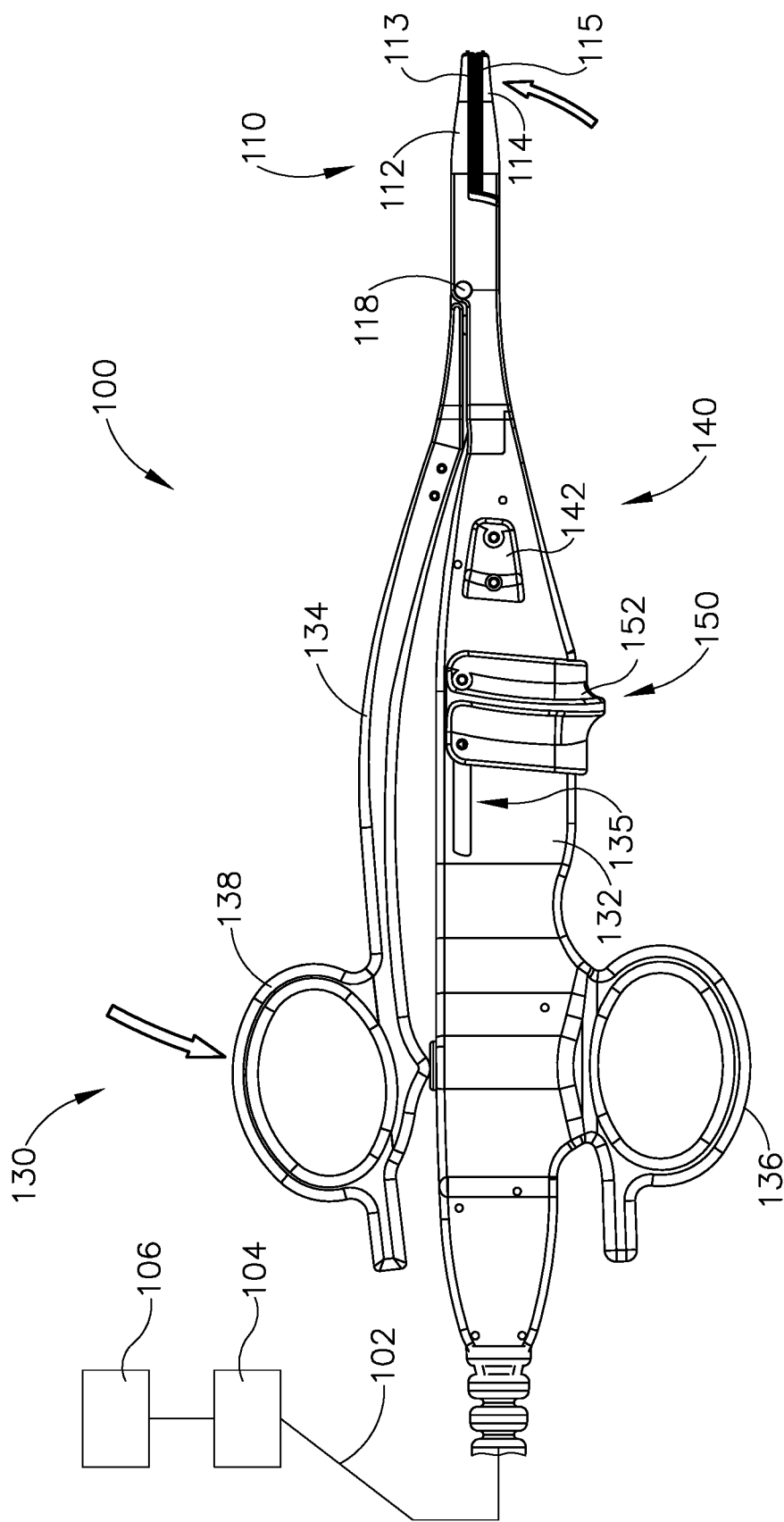
FIG. 3C depicts a side elevational view of the electrosurgical forceps instrument of FIG. 1, where the end effector is in the closed position, where the resilient arm is in a flexed position, and where the translating knife of FIG. 2 is in the proximal position.
Figure 3D:
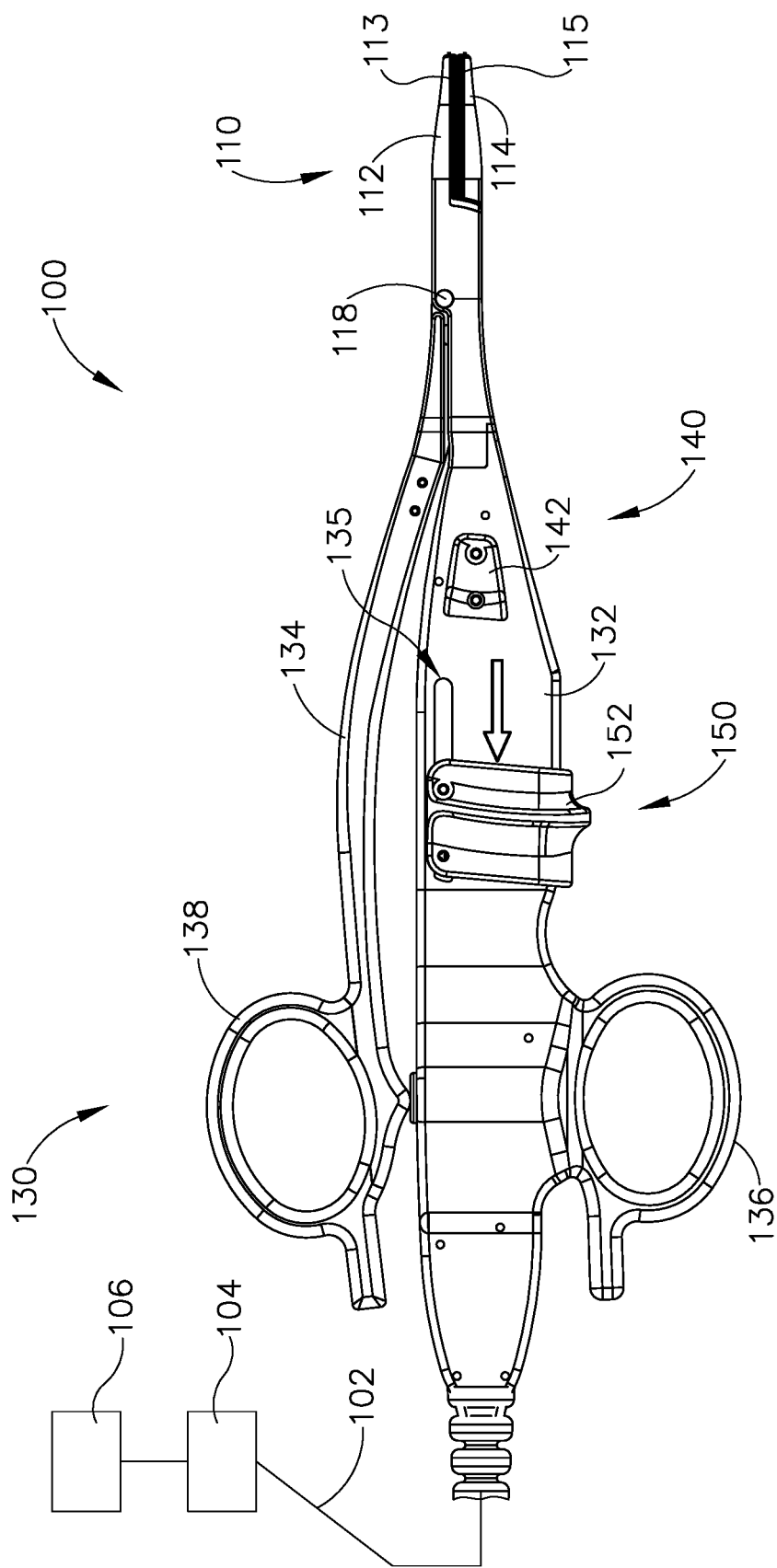
FIG. 3D depicts a side elevational view of the electrosurgical forceps instrument of FIG. 1, where the end effector is in the closed position, where the resilient arm is in the flexed position, and where the translating knife of FIG. 2 is in a distal position.

Next, as shown in FIG. 3C, if the operator desires to apply RF energy to grasped tissue, the operator may further pivot resilient arm (134) toward housing (132) such that resilient arm bends to the flexed position. As this point, the closure forces imparted on tissue by jaws (112, 114) is sufficient for proper sealing. The operator may then actuate RF trigger (142) such that electrodes (113, 115) provide RF energy to grasped tissue. Next, as shown between FIGS. 3C-3D and 4A-4B, the operator may desire to sever tissue captured between jaws (112, 114). Therefore, the operator may actuate trigger (152) proximally as shown between FIGS. 3C-3D such that knife (120) actuates distally as shown between FIGS. 4A-4B. Cutting edge (122) may sever tissue captures between jaws (112, 114) as knife (120) actuates distally through elongate slot (116).

While in the current example, the operator applies RF energy to grasped tissue and then subsequently severs the tissue, the operator may alternatively sever grasped tissue first, then apply RF energy to the tissue as would be apparent to one of ordinary skill in the art in accordance with the teachings herein. Alternatively, the operator may only seal grasped tissue by applying RF energy, without severing the tissue, as would be apparent to one of ordinary skill in the art in accordance with the teachings herein. Alternately, the operator may only sever grasped tissue, without sealing the tissue, as would be apparent to one of ordinary skill in the art in accordance with the teachings herein. Alternatively, the operator may just grasp tissue, without severing or sealing the tissue, as would be apparent to one of ordinary skill in the art in accordance with the teachings herein.

II. Alternative Exemplary Electrosurgical Forceps

As mentioned above, it may be desirable to have a compact firing assembly with a trigger close to the center of the housing such that it is easy to actuate the firing assembly regardless of whether the instrument is flipped. Therefore, it may be desirable to have various firing assemblies that are configured to convert proximal translation of a sliding trigger into distal translation of a knife in order to sever tissue.

As also mentioned above, resilient arm (134) may flex toward housing (132) when jaws (112, 114) are in the closed position to provide greater closure forces between jaws (112, 114). The closure forces provided by flexing resilient arm (134) may help activated electrodes (113, 115) properly seal tissue grasped between jaws (112, 114). During exemplary use, if the operator fails to generate enough closure force while jaws (112, 114) are in the closed position, electrodes (113, 115) may fail to properly seal tissue grasped between jaws (112, 114). Therefore, it may be desirable to provide a lockout assembly that indicates when jaws (112, 114) provide a suitable closure force for sealing grasped tissue or prevents electrodes (113, 115) from activating unless jaws (112, 114) provide a suitable closure force for sealing grasped tissue.

In some instances, the operator may accidentally actuate knife trigger (152) proximally while jaws (112, 114) are open, inadvertently exposing distal cutting edge (122) of knife (120) within slot (116). Therefore, it may be desirable to provide a lockout mechanism that prevents actuation of knife until jaws (112, 114) are sufficiently closed. Alternatively, the operator may properly actuate knife (120) distally while jaws (112, 114) are suitably grasping tissue, and then prematurely open jaws (112, 114) such that distal cutting edge (122) is inadvertently exposed within slot (116). Inadvertent exposure of distal cutting edge (122) within slot (116) while jaws (112, 114) are open may cause accidental tissue damage. Therefore, it may be desirable to prevent exposure of distal cutting edge (122) after distally firing knife (120) through jaws (112, 114) by having an automatic knife return mechanism configured to automatically drive knife (120) to a pre-fired position after knife (120) reaches a predetermined distal position.

While various examples of firing assemblies, lockout assemblies, and knife return mechanisms are described below, it should be understood various combinations or modifications may be made to such firing assemblies, lockout assemblies, and knife return mechanism as would be apparent to one having ordinary skill in the art in view of the teachings herein.

Figure 5:
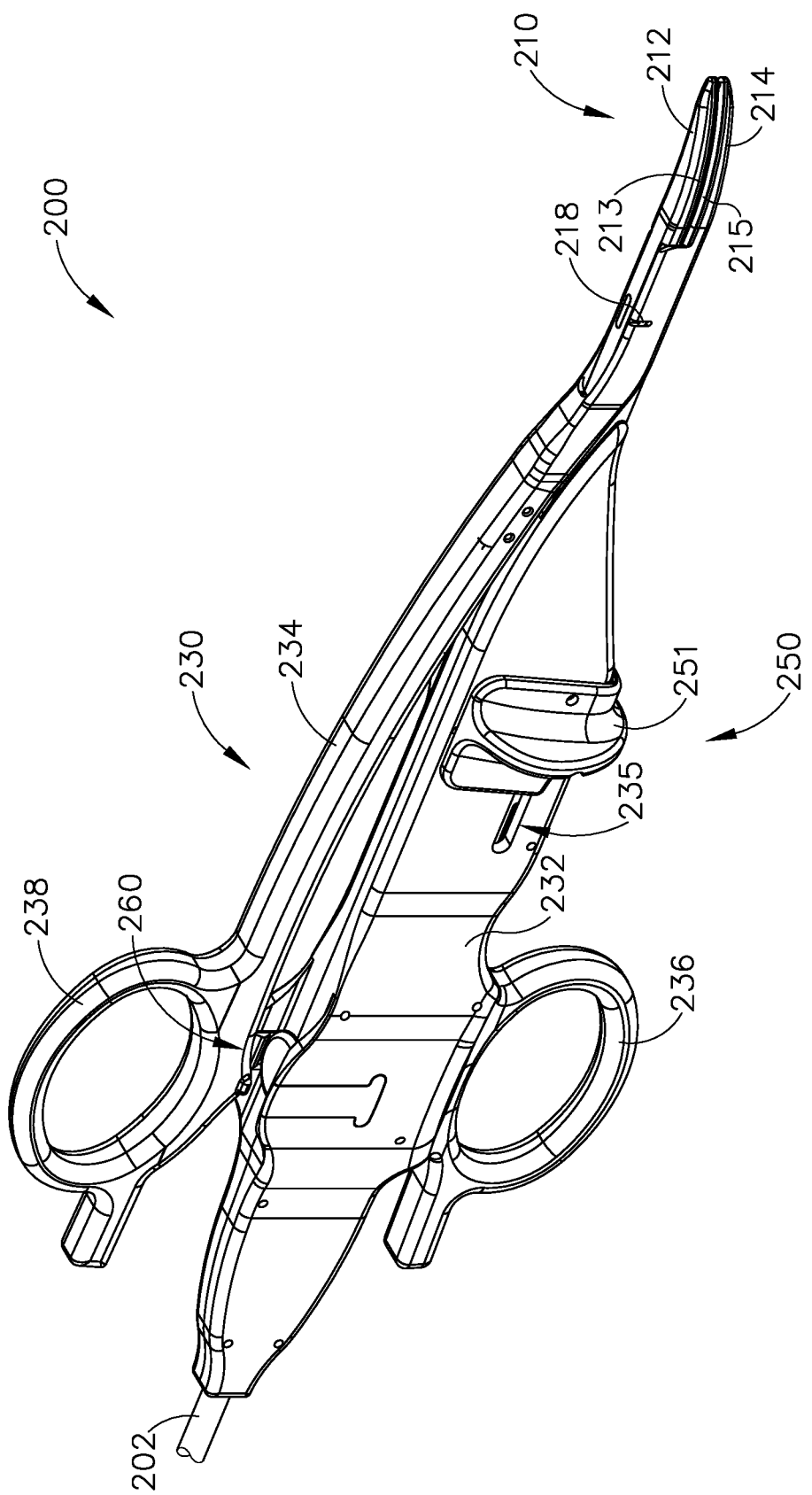
FIG. 5 depicts a perspective view of another exemplary electrosurgical forceps instrument, where an end effector is in a closed position, and where a resilient arm is in a relaxed position.

FIG. 5 shows an alternative exemplary electrosurgical forceps instrument (200) that may be used in replacement of instrument (100) described above. Therefore, as will be described in greater detail below, instrument (200) may be used to grasp, seal, and sever tissue.

Instrument (200) includes an end effector (210), a handle assembly (230), an electrode activation assembly (240), a firing assembly (250), and a lockout assembly (290). End effector (210) is substantially similar to end effector (110) described above, with differences elaborated below. End effector (210) includes a first jaw (212) having a first electrode (213), a second jaw (214) having a second electrode (215), and a knife (220) configured to translate through the first jaw (212) and the second jaw (214).

Figure 6:
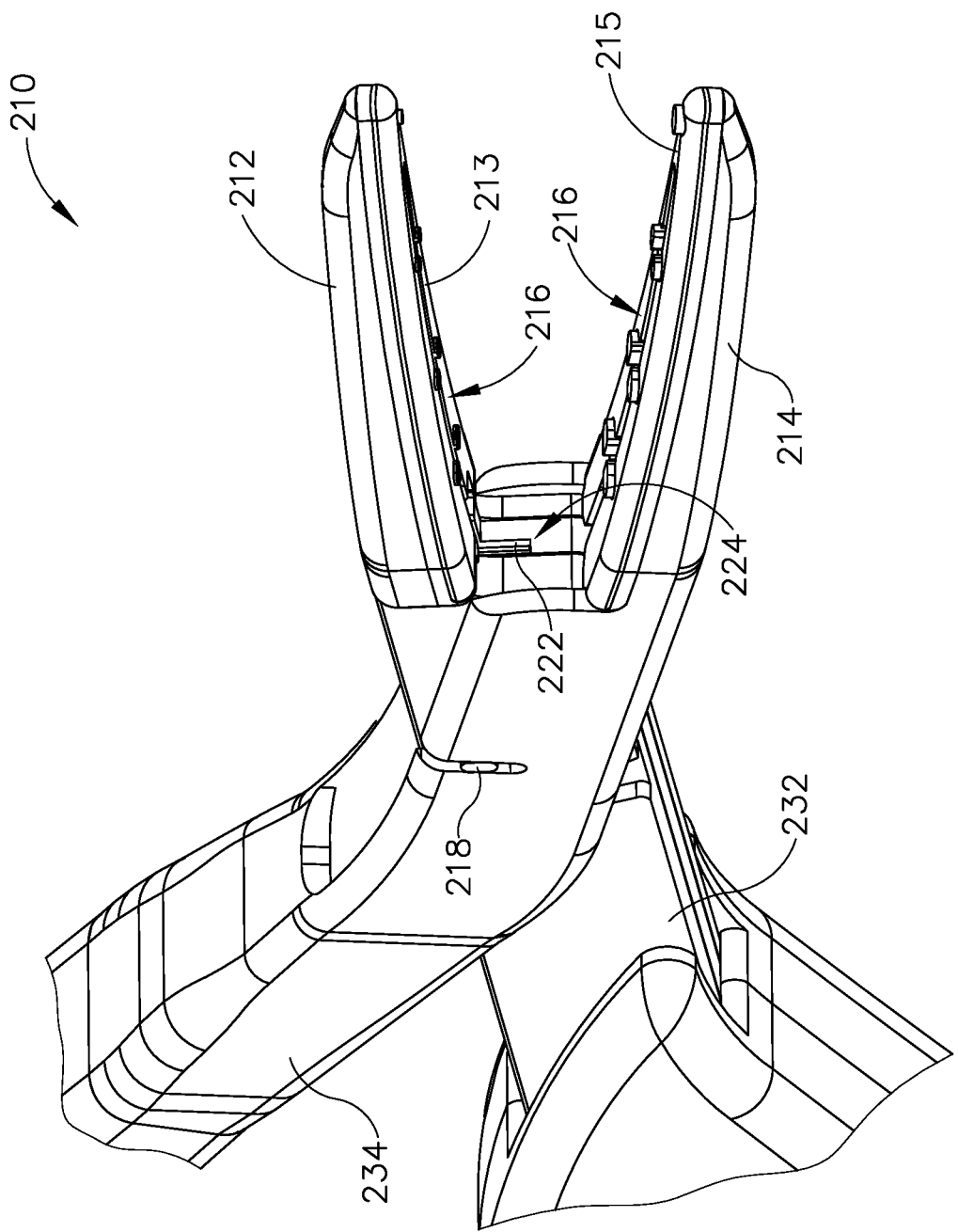
FIG. 6 depicts a perspective view of the end effector of FIG. 5 in an opened position, where a translating knife is in a proximal position.
Figure 7:
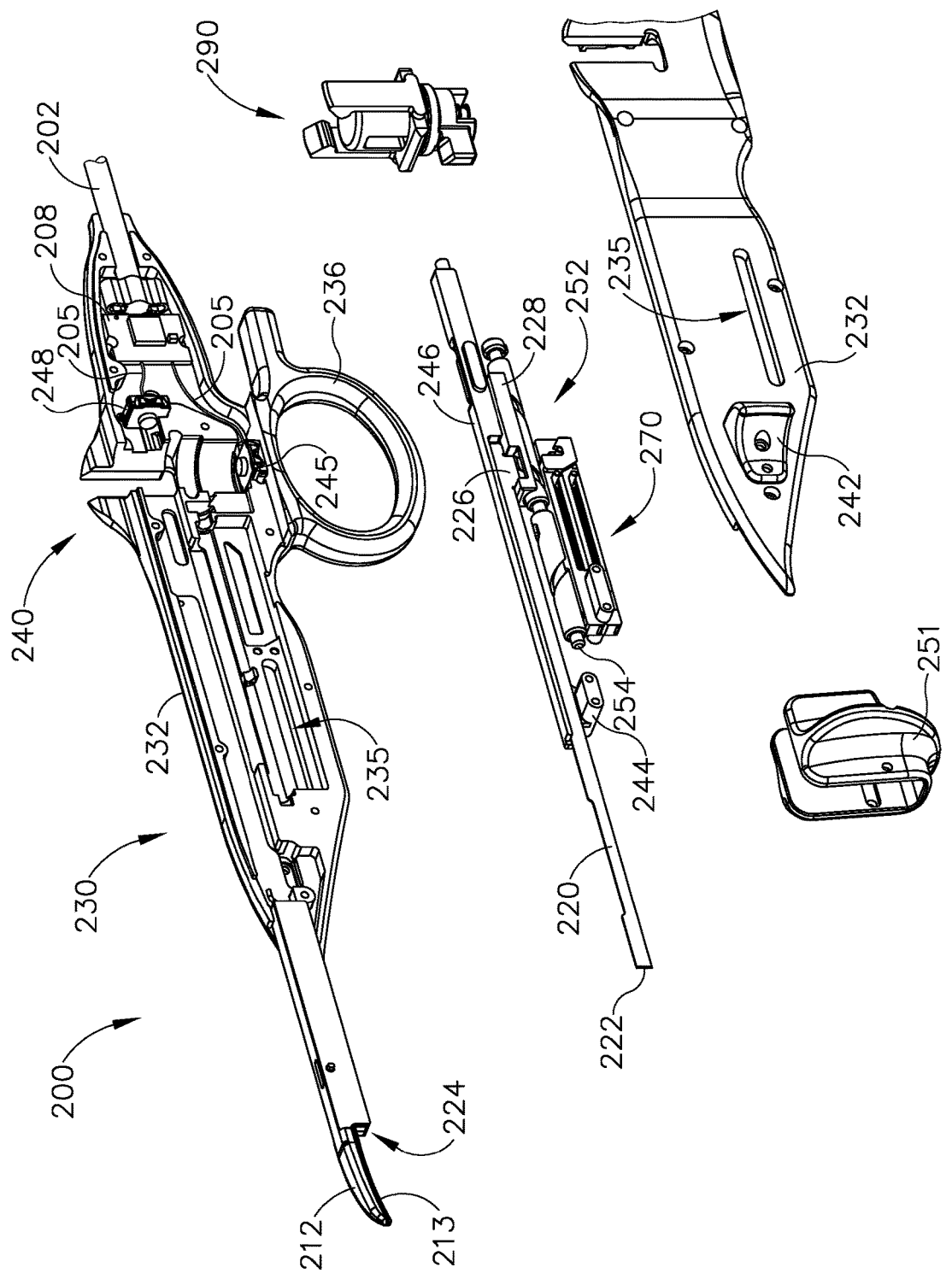
FIG. 7 depicts an exploded perspective view of a handle assembly of the electrosurgical forceps instrument of FIG. 5.
Figure 8:
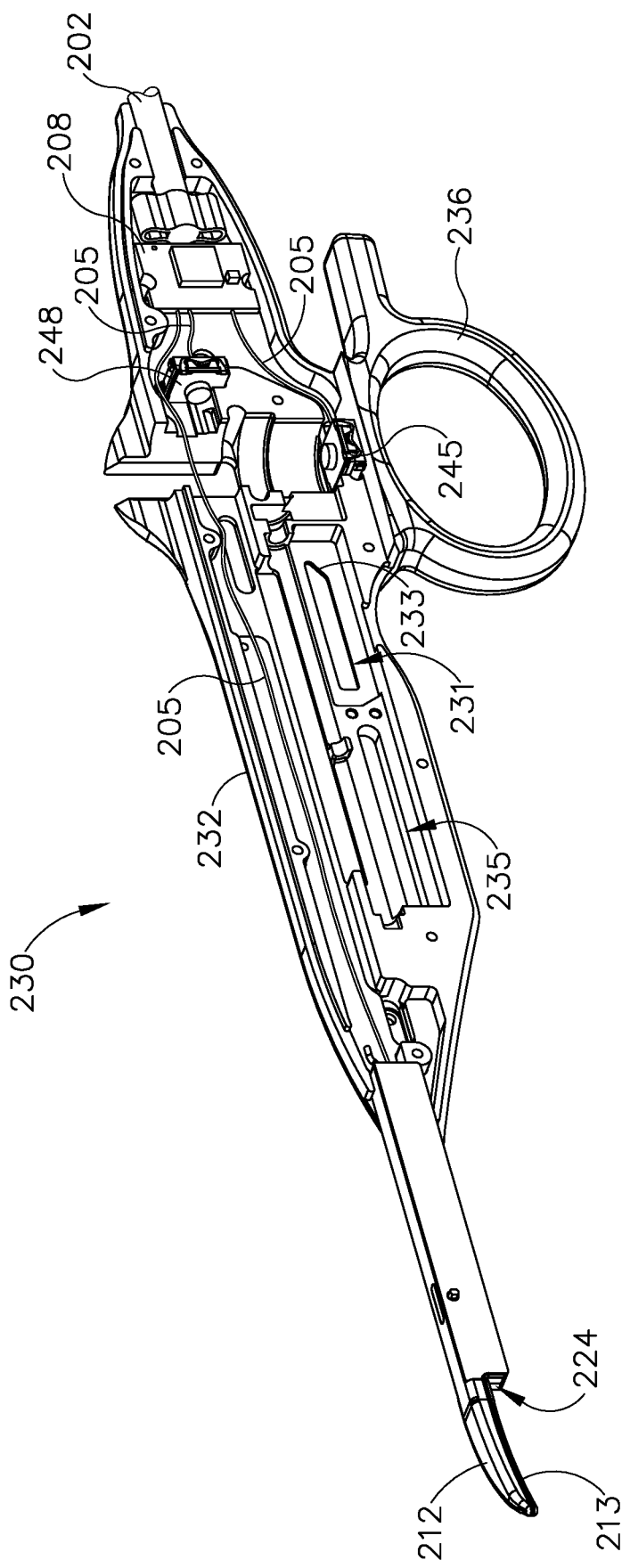
FIG. 8 depicts a perspective view of a portion of the handle assembly of FIG. 7.
Figure 11:
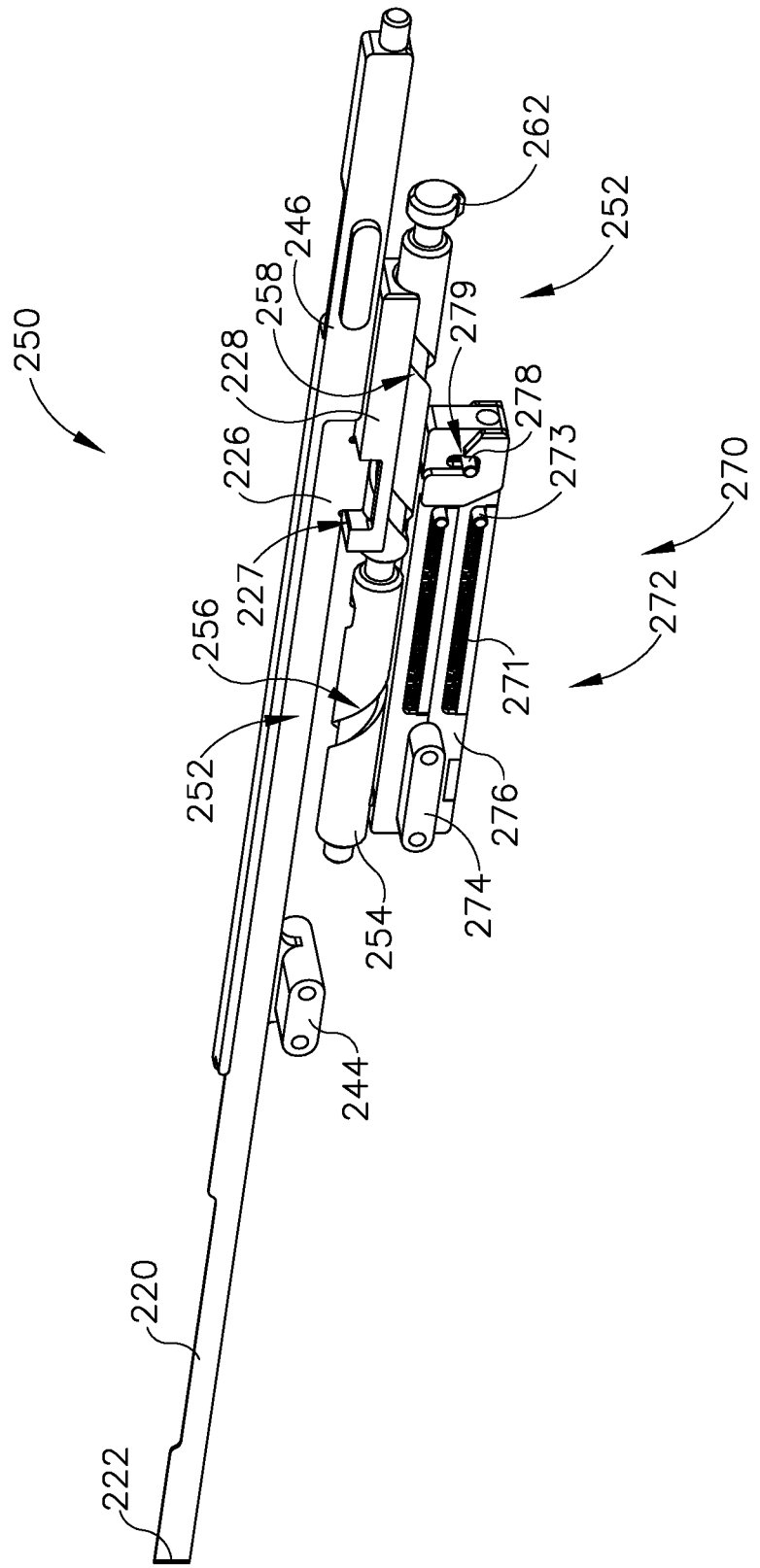
FIG. 11 depicts a perspective view of a firing assembly of the electrosurgical forceps instrument of FIG. 5.
Figure 12:
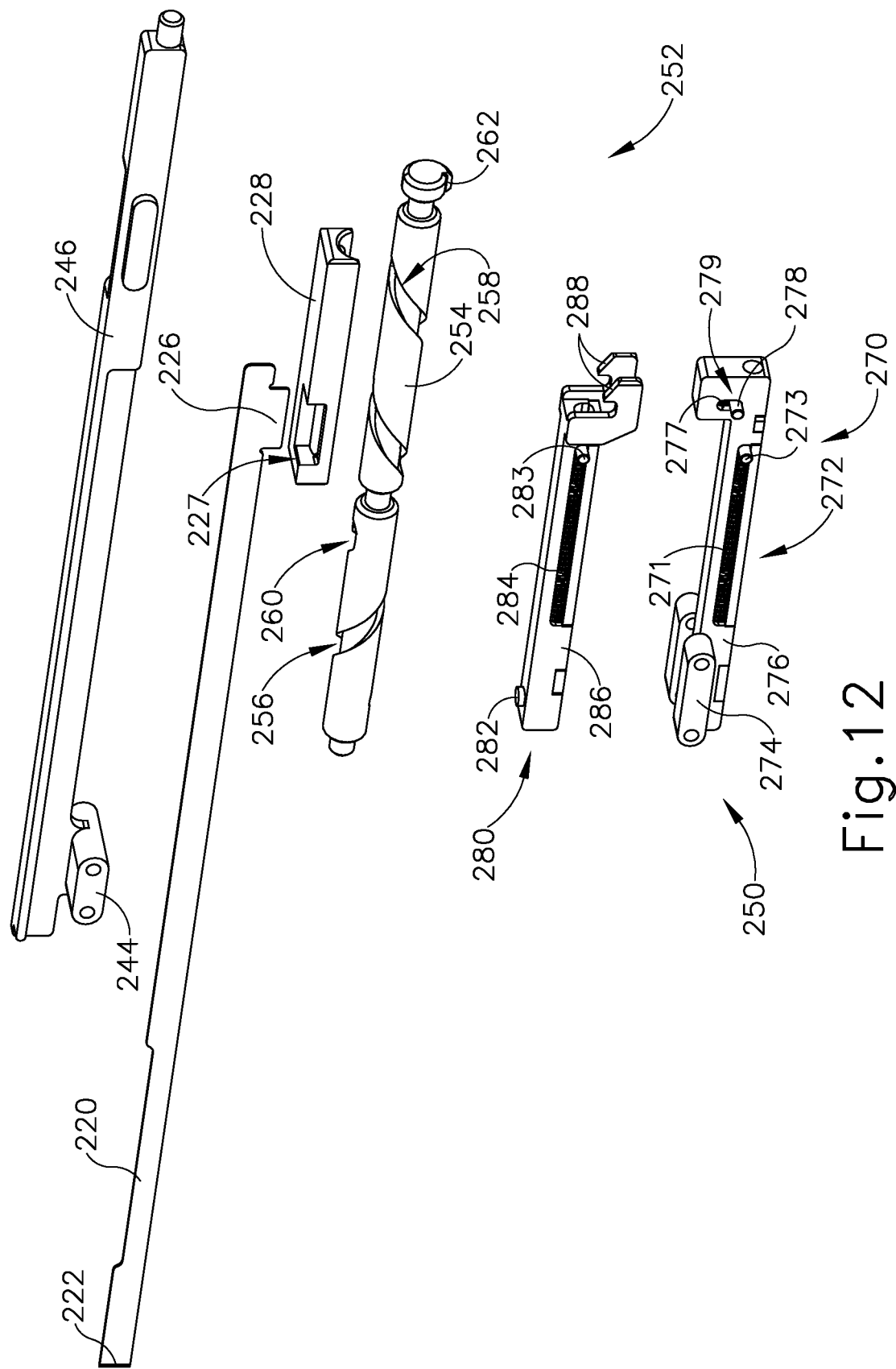
FIG. 12 depicts an exploded perspective view of the firing assembly of FIG. 11.

First jaw (212) and second jaw (214) are pivotably coupled with each other via pivot pin (218). First jaw (212) and second jaw (214) may pivot between an open position (FIG. 6) and a closed position (FIG. 5) in order to grasp tissue. First and second electrodes (213, 215) are positioned on respective jaws (212, 214) such that electrodes (213, 215) face each other when jaws (212, 214) are pivoted into the closed position. Additionally, each electrode (213, 215) is U-shaped in the present example, with the bend of the U-shape located near the distal end of each respective jaw (212, 214), such that each electrode (213, 215) includes two longitudinally extending, laterally spaced-apart legs extending along the length of each respective jaw (212, 214). Laterally spaced-apart legs of each electrode (213, 215) and corresponding portions of jaws (212, 214) define an elongate slot (216). Elongate slot (216) is dimensioned to slidably receive knife (220) such that knife may translate from a proximal position to a distal position, similar to knife (120) described above. As best shown in FIGS. 7, 11, and 12, knife (220) includes a distal cutting edge (222) configured to sever tissue captured between jaws (212, 214) in the closed position.

A cable (202) extends proximally from handle assembly (230). Similar to cable (102) of instrument (100), cable (202) is configured to couple with control unit (104), which is further coupled with a power source (106). Therefore, control unit (104) is operable to provide RF power to electrodes (213, 215) of jaws (212, 214), to thereby seal tissue suitably captured between jaws (212, 214).

Handle assembly (230) includes a housing (232) and a resilient arm (234). Housing (232) and resilient arm (234) are substantially similar to housing (122) and resilient arm (134) described above, with differences elaborated below. Housing (232) and resilient arm (234) are pivotably coupled with each other via pivot pin (218). Housing (232) extends distally into first jaw (212), while resilient arm (234) extends distally into second jaw (214). Housing defines a knife pathway (224) that slidably houses a portion of knife (220). Housing (232) includes a finger ring (236) while resilient arm (234) terminates proximally into a thumb ring (238). Therefore, the operator may grasp instrument (200) in a scissor grip fashion and pivot resilient arm (234) relative to housing (232) via rings (236, 238) in order to open and close jaws (212, 214).

Resilient arm (234) is substantially similar to resilient arm (134) described above. Therefore, resilient arm (234) is sufficiently resilient such that arm (234) may flex from a relaxed position to a flexed position in response to pivoting arm (234) further toward housing (232) when jaws (212, 214) are already in the closed position. Resilient arm (234) is biased toward the relaxed position. Further pivoting of resilient arm (234) into the flexed position may result in greater closure forces between jaws (212, 214) as compared to pivoting jaws (212, 214) into the closed position while arm (234) is in the relaxed position. Resilient arm (234) may be suitably resilient such that when resilient arm (234) is pivoted into the flexed position, the closure force between jaws (212, 214) is sufficient such that electrodes (213, 215) may properly seal tissue grasped between jaws (212, 214). Additionally, the resilient nature of arm (234) may limit the amount of closure force between jaws (212, 214) such that jaws (212, 214) may not compress tissue too much, resulting in inadvertent tissue damage. When the operator no longer desires to compress tissue between jaws (212, 214) to properly seal or sever clamped tissue, the operator may reduce the amount of closure force applied to resilient arm (234) such that arm (234) returns to the relaxed state.

Housing (232) contains electrode activation assembly (240), firing assembly (250), and lockout assembly (290). Firing assembly (250) of the current example includes a knife trigger (251) slidably coupled with housing (232) via a slot (235). As will be described in greater detail below, electrode activation assembly (240) is configured to selectively activate electrodes (213, 215); firing assembly (250) is configured to actuate knife (220) between the proximal position and the distal position (Similar to knife (120) as shown in FIGS. 4A-4B) in response to proximal translation of knife trigger (251) within slot (235); and lockout assembly (290) is configured to prevent actuation of knife (220) until specific conditions are satisfied. In some examples, lockout assembly (290) may be configured to prevent activation of electrodes (213, 215) until specific conditions are satisfied, or indicate when jaws (212, 214) are sufficiently closed for suitably sealing tissue. As will also be described in greater detail below, a portion of firing assembly (250) and handle assembly (230) form an automatic knife return mechanism configured to automatically drive knife (220) to the proximal, pre-fired, position after knife (220) reaches a predetermined distal position.

Electrode activation assembly (240) includes an RF trigger (242) slidably supported on each lateral side of housing (232), a sliding body (246) slidably contained within housing (232), a coupling block (244) fixed relative to sliding body (246), an activation button (248), and a lockout button (245). Coupling block (244) is configured to couple with each RF trigger (242) when instrument (200) is assembled. A proximal end of sliding body (246) is directly adjacent to activation button (248) such that proximal translation of sliding body (246) triggers activation button (248). Therefore, the operator may press RF trigger (242) proximally in order to compress activation button (248). RF trigger (242), coupling block (244), and/or sliding body (246) may be biased toward a position such that activation button (238) is not activated.

Activation button (248) and lockout button (245) are each contained within housing (232). Lockout button (245) and activation button (248) are each in communication with a circuit board (208) via electrical coupling wires (205); while circuit board (208) is also in communication with at least one electrode (213, 215) via electrical coupling wires (205). In the present example, circuit board (208) is contained within housing (232). Circuit board (208) is in communication with cable (202) such that circuit board (208) and control unit (104) are in electrical communication with each other. Therefore, circuit board (208) is configured to transfer RF energy from control unit (104) to electrodes (213, 215). As will be described in greater detail below, lockout assembly (290) is configured to depress lockout button (245) when jaws (212, 214) are sufficiently closed to provide sufficient closure force to properly seal tissue captured between electrodes (213, 215) using RF energy.

In one example, activation button (248) and lockout button (245) are configured to instruct circuit board (208) to transfer RF energy from control unit (104) to electrodes (213, 215) when buttons (245, 248) are depressed. If only one, or neither, button (245, 248) is depressed, circuit board (208) will not transfer RF energy to electrodes (213, 215), thereby leaving electrodes (213, 215) deactivated. Therefore, for example, if the operator pressed RF trigger (242) without having lockout button (245) depressed, electrodes (213, 215) will remain deactivated. Alternatively, lockout button (245) may act as a switch for activation button (248) such that activation of lockout button (245) completes a circuit between at least one electrode (213, 215) and activation button (248).

In another example, lockout button (245) may only generate a signal to circuit board (208), which may then send the signal to control unit (104), that jaws (212, 214) are sufficiently closed to provide sufficient closure force to properly seal tissue captured between electrodes (213, 215) using RF energy. Control unit (104) may then signal to the operator (i.e. visually, audibly, or tactilely) that jaws (212, 214) are sufficiently closed. In such examples, activation button (248) may independently instruct circuit board (208) to transfer RF energy from control unit (104) to electrodes (213, 215) when activation button (248) is depressed.

In another example, depression of either activation button (248) or lockout button (245) may be configured to activate electrodes (213, 215), but activation of buttons (245, 248) may send a different signal to control unit (104), such that control unit produces a different signal (i.e. visually, audibly, or tactilely) indicating to a user which button (245, 248) has been depressed.

In yet another example, activation button (248) may be omitted entirely such that pressing lockout button (245) leads to activation of electrodes (213, 215).

While in the current example, circuit board (208) acts as an intermediary between control unit (104), electrodes (213, 215), and buttons (245, 248), this is merely optional, as buttons (245, 248) and electrodes (213, 215) may be in communication with cable (202) and control unit (104) without the use of circuit board (208).

Figure 9:
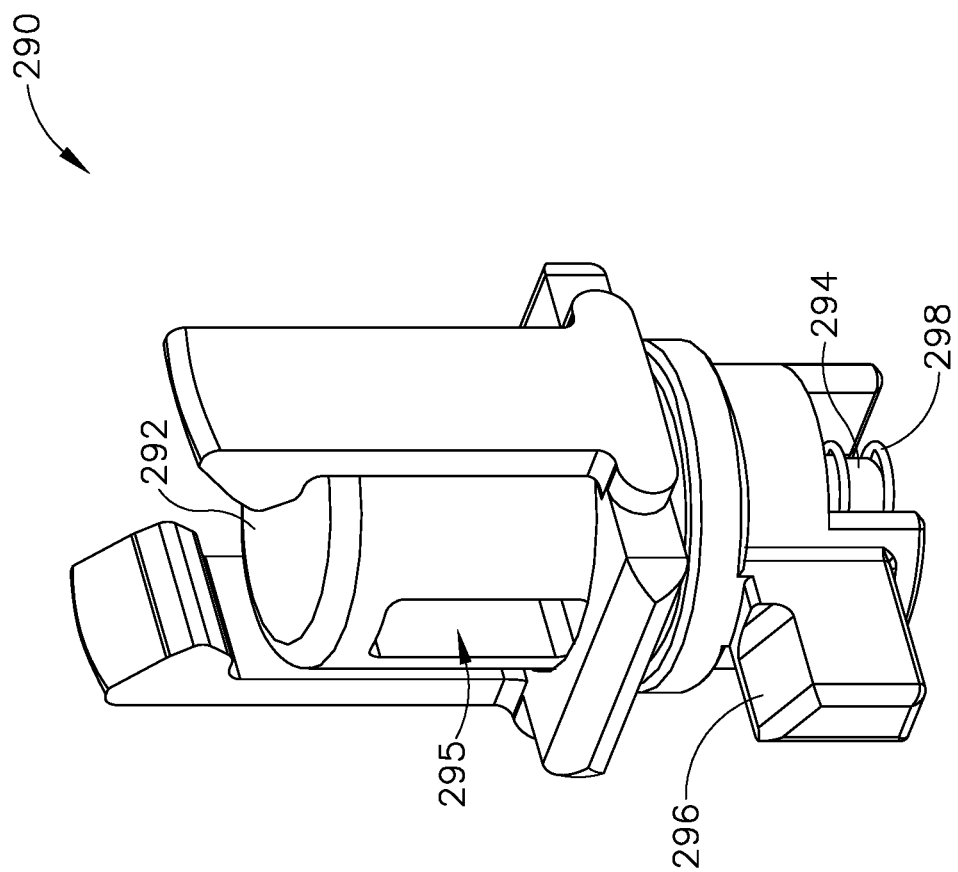
FIG. 9 depicts a perspective view of a lockout assembly of the electrosurgical forceps instrument of FIG. 5.
Figure 10:
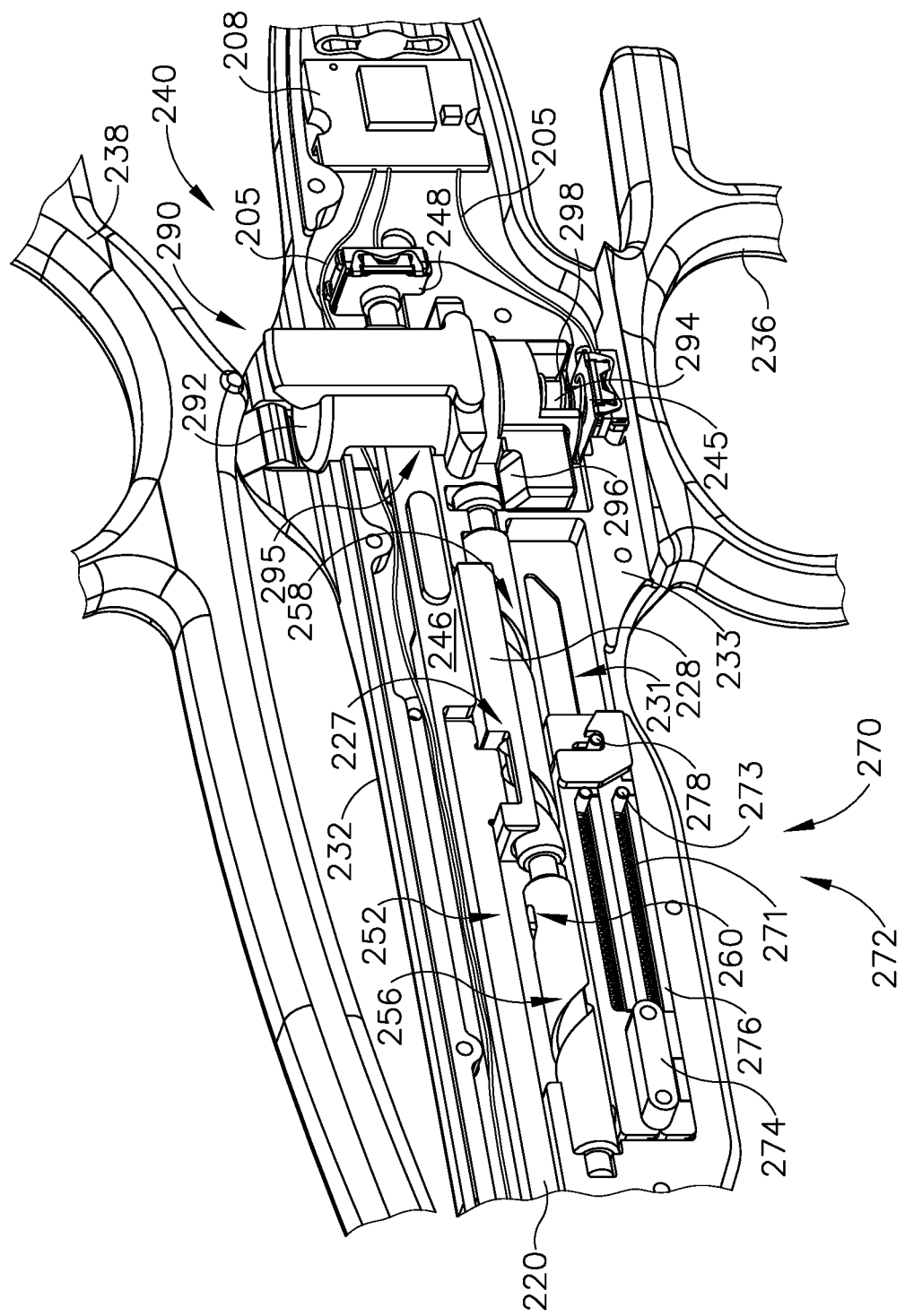
FIG. 10 depicts a perspective view of a portion of the forceps instrument of FIG. 5, with a portion of the handle assembly of FIG. 7 omitted for clarity, where the lockout assembly of FIG. 9 is in a locked configuration, and where the resilient arm is in the relaxed position.

As mentioned above, lockout assembly (290) is configured to either indicate when jaws (212, 214) are sufficiently closed or prevent activation of electrodes (213, 215) until jaws (212, 214) are sufficiently closed; while lockout assembly (290) is also configured to prevent actuation of knife (220) until specific conditions are satisfied. As best seen in FIGS. 9-10, lockout assembly (290) includes a translating body (292) defining a through hole (295), and a bias spring (298). Translating body (292) includes a button (294) extending downwardly from the rest of body (292), and a lockout ledge (296) extending distally from the rest of body (292). Translating body (292) is slidably disposed within housing (232). Translating body (292) is configured to actuate between a locked position (as shown in FIGS. 10 and 15A) to an unlocked position (as shown in FIGS. 15B-15F); while bias spring (298) abuts against an interior portion of housing (132) and translating body (292) to bias translating body (292) toward the locked position.

Figure 15A:
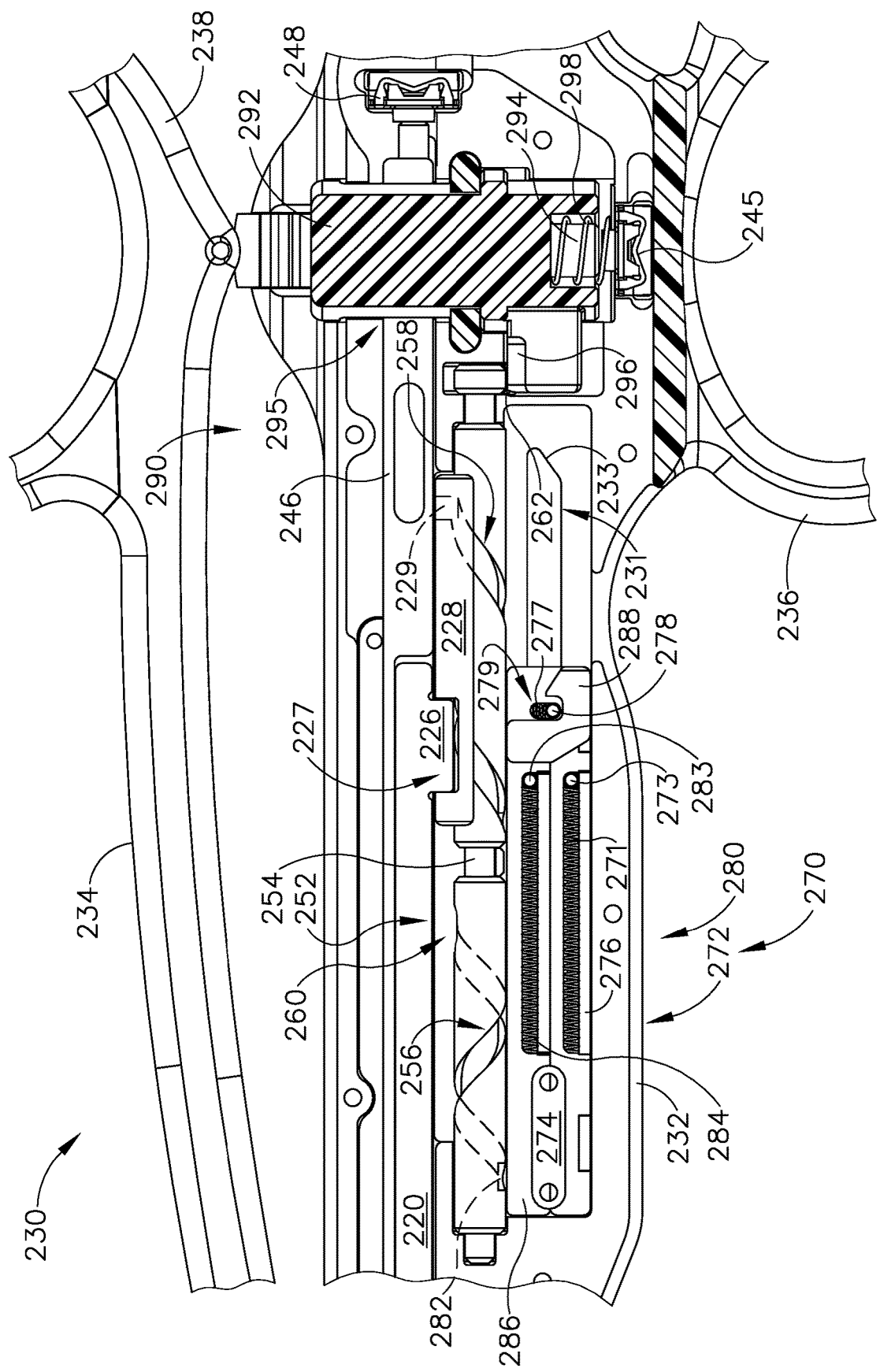
FIG. 15A depicts a side elevational view of a portion of the instrument of FIG. 5, with a portion of the handle assembly of FIG. 7 omitted for clarity, where the end effector is in the closed position, where the resilient arm is in a relaxed position, where the lockout assembly of FIG. 9 is in a locked configuration, and where the firing assembly of FIG. 11 is in a first pre-fired position.

As best seen in FIGS. 10 and 15A, a portion of translating body (292) extends away from housing (232) toward thumb ring (238) while in the locked position. Thumb ring (238) of resilient arm (234) is dimensioned to abut against the portion of translating body (292) extending away from housing (232) when resilient arm (234) is in the flexed position, thereby driving lockout assembly (290) into the unlocked position. Thumb ring (238) does not abut against the portion of translating body (292) extending away from housing (232) when resilient arm (234) is in the relaxed position, such that spring (298) biases translating body (292) into the locked position.

As described above, the closure forces provided by jaws (212, 214) when resilient arm (234) is in the flexed position are suitable for electrodes (213, 215) to seal tissue via RF energy. Therefore, lockout assembly (290) is configured to move into the unlocked position when jaws (212, 214) provide a suitable closure force for electrodes (213, 215) to seal tissue via RF energy. Additionally, lockout assembly (290) is configured to move into the locked position when jaws (212, 214) do not provide a suitable closure force for electrodes (213, 215) to seal tissue via RF energy.

While in the unlocked position, button (294) depresses lockout button (245) of electrode activation assembly (240), thereby rendering lockout button (245) activated. Therefore, in one example, if the operator presses RF trigger (242) while lockout assembly (290) is in the unlocked position, circuit board (208) would activate electrodes (213, 215) dues to both buttons (248, 245) being depressed. In other words, the operator is permitted to activate RF energy to electrodes (213, 215) when the closure forces provided by jaws (212, 214) are suitably conducive for sealing tissue via RF energy. In another example, lockout button (245) generates a signal send to control unit (104). An in yet another example, depressing lockout button (245) instructs circuit board (208) to activate electrode (213, 215).

Also, while in the unlocked position, lockout ledge (296) is spaced away from an angular locking body (262) of firing assembly (250) such that firing assembly (250) may actuate knife (220) in accordance with the description herein. Therefore, when lockout assembly (290) is in the unlocked position, the operator may both activate electrodes (213, 215) with RF energy, and actuate knife (220) distally to sever tissue grasped between jaws (212, 214). Lockout assembly (290) may indicate to the operator when lockout assembly (290) is in the unlocked configuration. For example, depressing button (245) may activate a suitable indicator as would be apparent to one having ordinary skill in the art in view of the teachings herein. For example, an LED may turn on, an instrument may emit noise, or a tactile response may be felt.

While in the locked position, button (294) is spaced away from lockout button (245) of electrode activation assembly (240), thereby rendering lockout button (245) un-activated. Therefore, in the example where both lockout button (245) and activation button (248) must be depressed to activate electrodes (213, 215), if the operator presses RF trigger (242) while lockout assembly (290) is in the locked position, either accidentally or in an attempt to provide RF energy to electrodes (213, 215), circuit board (208) would not activate electrodes (213, 215) due to both buttons (248, 245) not being depressed. In other words, the operator is prevented from activating RF energy to electrodes (213, 215) when the closure forces provided by jaws (212, 214) are not suitably conducive for sealing tissue via RF energy (i.e. resilient arm (234) is in the relaxed position).

Also, while in the locked position, lockout ledge (296) is directly adjacent to angular locking body (262) of firing assembly (250), thereby preventing actuation of firing assembly (250) while body (292) is in the locked position. As will be described in greater detail below, angular locking body (262) is fixed to a rotary drive assembly (252) configured to rotate in order to distally translate knife (220). Since lockout ledge (296) prevents rotation of angular locking body (262) while lockout assembly (290) is in the locked position, lockout ledge (296) also prevents distal translation of knife (220) while lockout assembly (290) is in the locked position. In other words, when lockout assembly (290) is in the locked position, the operator may be prevented from activating electrodes (213, 215) with RF energy, as well as prevented from distally actuating knife (220) to sever tissue.

Through hole (295) is dimensioned to allow suitable portions of electrode activation assembly (240) to actuate within through holes (295). In the current example, one through hole (295) allows sliding body (246) of electrode activation assembly (240) to actuate within through hole (295) to access activation button (248).

As mentioned above, firing assembly (250) is configured to convert proximal translation of trigger (251) into distal translation of knife (220). As also mentioned above, a portion of firing assembly (250) and handle assembly (230) form an automatic knife return mechanism configured to automatically drive knife (220) to a pre-fired position after knife (220) reaches a predetermined distal position. Firing assembly (250) includes an input drive assembly (270), a rotary drive assembly (252), and an output drive assembly, such as output drive body (228) coupled with a proximal body (226) of knife (220). As will be described in greater detail below, trigger (251) is configured to actuate input drive assembly (270) proximally such that rotary driver assembly (252) actuates output drive body (228) and knife (220) distally. It should be understood that sliding body (246) of electrode activation assembly (240) may slide independently relative to firing assembly (250). Therefore, the operator may activate electrodes (213, 215) independently of firing assembly (250) and knife (220), in accordance with the description herein.

Input drive assembly (270) includes a first sliding member (272) and a second sliding member (280). Both sliding members (272, 280) are slidably contained within housing (232). As will be described in greater detail below, first sliding member (272) is configured to proximally drive second sliding member (280), while second sliding member (280) is configured to actuate rotary drive assembly (252).

As best seen in FIG. 11, first sliding member (272) includes a coupling block (274), a sliding body (276), a transverse driving pin (278), a grounding pin (273), a first biasing member (271) disposed within the confines of sliding body (276) against grounding pin (273), and a second biasing member (277) housed within a slot (279) defined by sliding body (276). Sliding body (276) is slidably contained within housing (232) such that sliding body (276) may translate within housing (232) but may not rotate relative to housing (232). Coupling block (274) is fixed relative to sliding body (276). Coupling block (274) is configured to couple with trigger (251) when instrument (200) is assembled such that actuation of trigger (251) relative to housing (232) drives actuation of coupling block (274) and sliding body (276) relative to housing (232).

Figure 15B:
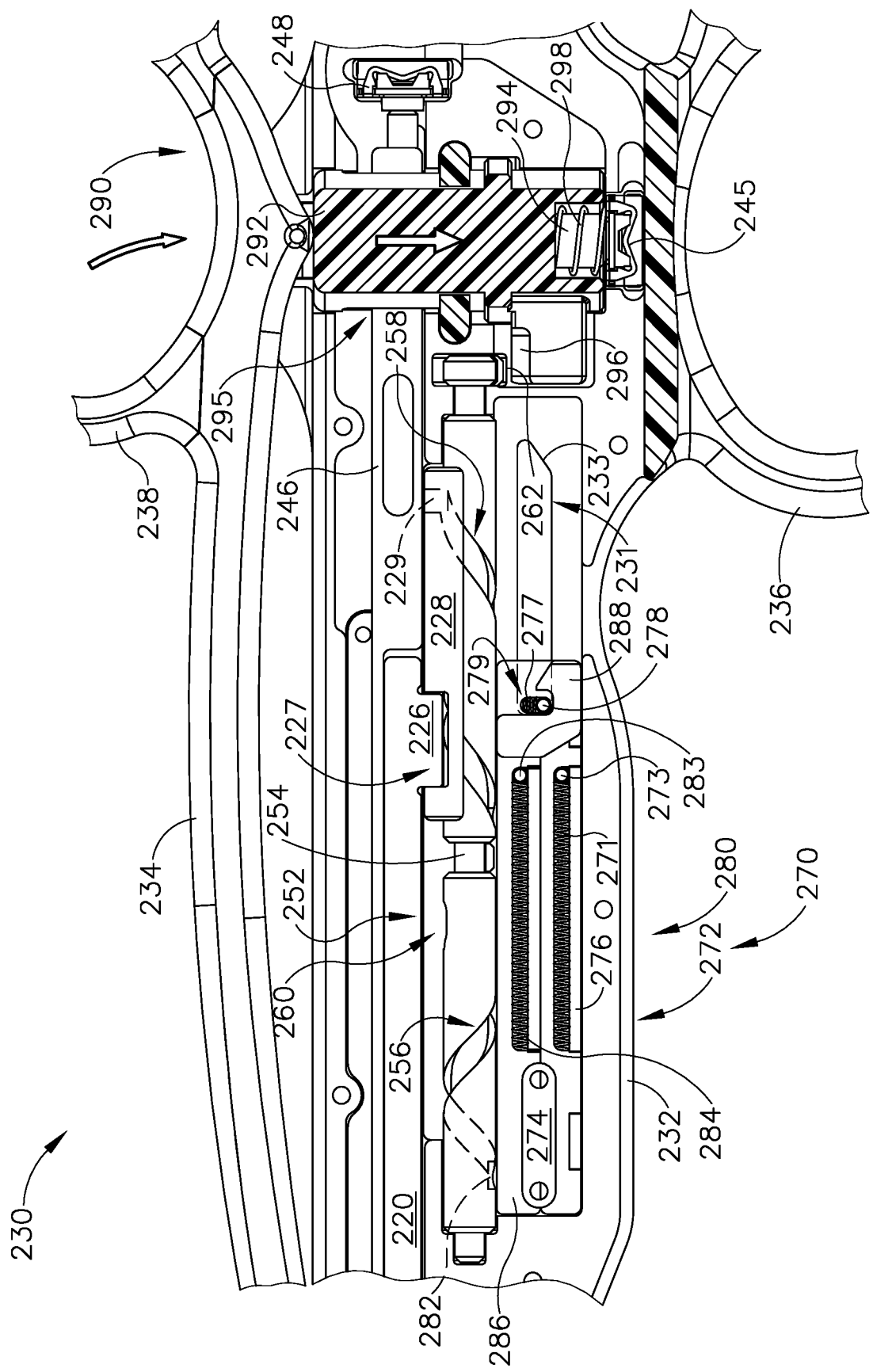
FIG. 15B depicts a side elevational view of a portion of the instrument of FIG. 5, with a portion of the handle assembly of FIG. 7 omitted for clarity, where the end effector is in the closed position, where the resilient arm is in a flexed position, where the lockout assembly of FIG. 9 is in an unlocked configuration, and where the firing assembly of FIG. 11 is in the first pre-fired position.

As will be described in greater detail below, transverse driving pin (278) is dimensioned to drive portions of second sliding member (280) proximally in response to proximal translation of first sliding member (272). As will also be described in greater detail below, transverse driving pin (278) is slidable within slot (279) such that transverse driving pin (278) may selectively disassociate with second sliding member (280) such that second sliding member (280) automatically returns to a distal position associated with knife (220) being in a pre-fired position. Grounding pin (273) is fixed to housing (232) when instrument (200) is assembled such that as sliding body (276) translates, grounding pin (273) remains spatially fixed relative to housing (232). Biasing member (271) abuts against grounding pin (273) and sliding body (276) in order to bias sliding body (276) to a distal, pre-fired position (as shown in FIGS. 15A-15B and 15F). Therefore, if the operator actuates trigger (251) and sliding body (276) proximally, biasing member (271) compresses such that when the operator releases trigger (251), biasing member (271) actuates trigger (251) back to the distal, pre-fired, position. In the current example, biasing member (271) includes a spring, but any other suitable biasing member (271) may be used as would be apparent to one having ordinary skill in the art in view of the teachings herein.

Second sliding member (280) includes an input projection (282), a sliding body (286), a grounding pin (283), a biasing member (284) disposed within the confines of sliding body (286), and a pair of hooked, laterally spaced, projections (288). Input projection (282) and laterally spaced projections (288) are fixed to each other via sliding body (286). Sliding body (286) is slidably contained within housing (232) such that sliding body (286) may translate within housing (232) but may not rotate relative to housing (232). As will be described in greater detail below, projections (288) are dimensioned to abut against transverse driving pin (278) such that first sliding member (272) may proximally drive second sliding member (280). As will also be described in greater detail below, input projection (282) is configured to mesh with portions of rotary drive assembly (252) such that translation of input projection (282) rotates rotary drive assembly (252). Grounding pin (283) is fixed to housing (232) when instrument (200) is assembled such that as sliding body (286) translates, grounding pin (283) remains spatially fixed relative to housing (232). Biasing member (284) abuts against grounding pin (283) and sliding body (286) in order to bias sliding body (286) to a distal, pre-fired position (as shown in FIGS. 15A-15B, and 15F).

As mentioned above, sliding body (276) defines a slot (279) that slidably houses transverse driving pin (278). Second biasing member (277) biases transverse driving pin (278) to a downward position within slot (279). Transverse driving pin (278) may actuate within slot (279) to overcome the biasing force of second biasing member (277). Transverse driving pin (278) is dimensioned to abut against projections (288) of first sliding member (272) when second biasing member (277) biases transverse driving pin (278) in the downward position. Therefore, if the operator actuates trigger (251) proximally, first sliding member (272) may proximally drive second sliding member (280) via projections (288) and transverse driving pin (278). Additionally, as best shown in FIGS. 15A-15F, transverse driving pin (278) is housed within a slotted pathway (231) defined by the interior of housing (232). Therefore, as transverse driving pin (278) drives projections (288), a portion of pin (278) is within slotted pathway (231). As will be described in greater detail below, once first and second sliding members (272, 280) proximally translate a predetermined distance, transverse driving pin (278) may actuate within slot (289), due to contact with a cam surface (233) of slotted pathway (231), such that transverse driving pin (278) no longer engages projections (288). Therefore, with projections (288) no longer engaged with driving pin (278), first biasing member (284) may distally drive sliding body (286) and input protection (282) back to the distal, pre-fired position, which in turn may rotate rotary drive assembly (252).

Figure 14:
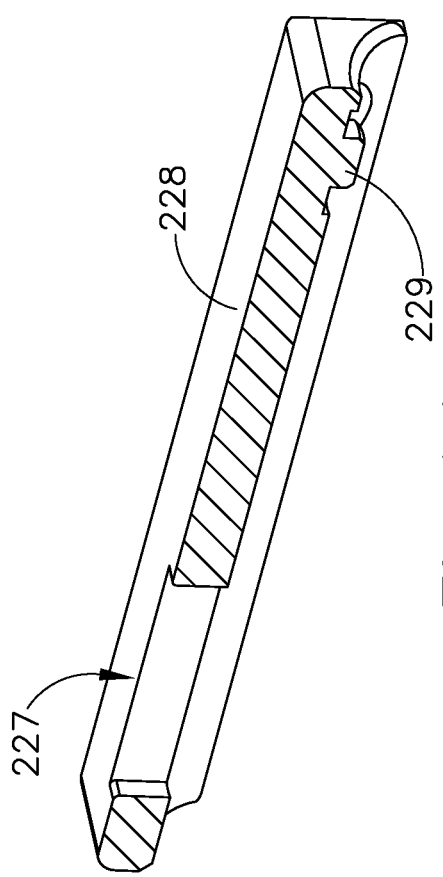
FIG. 14 depicts a cross-sectional perspective view of an output drive body of the firing assembly of FIG. 11.

As best shown in FIG. 14, output drive body (228) includes an output projection (229). Additionally, output drive body (228) defines a cutout (227) dimensioned to receive proximal body (226) of translating knife (220). Therefore, when instrument (200) is assembled, output drive body (228) and translating knife (220) may actuate relative to housing (232) together. Output drive body (228) is slidably contained within housing (232) such that output drive body (228) may translate relative to housing (232) but not rotate relative to housing (232). As will be described in greater detail below, output projection (229) is configured to mesh with a portion of rotary drive assembly (252) such that rotation of rotary drive assembly (252) longitudinally translates output drive body (228) and knife (220).

Figure 13:
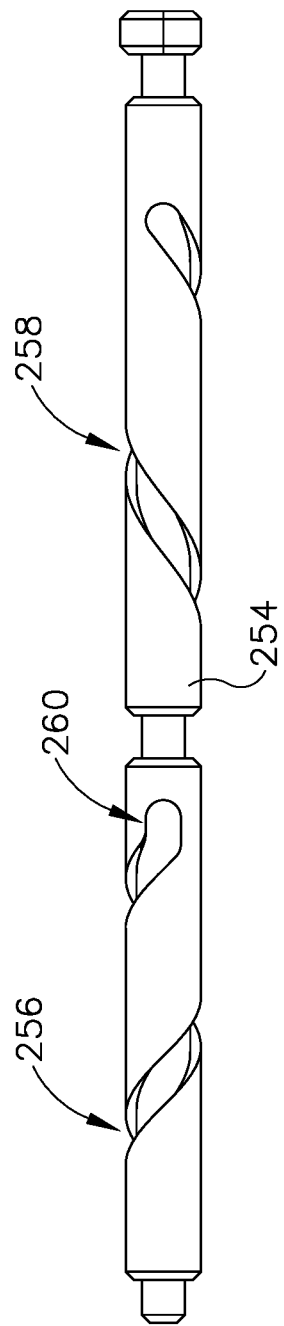
FIG. 13 depicts a top plan view of an opposed threaded body of the firing assembly of FIG. 11.

As best shown in FIGS. 12-13, rotary drive assembly (252) includes a threaded body (254) rotatably disposed within housing (232). Threaded body (254) may rotate about its own longitudinal axis within housing (232); but is otherwise fixed relative to housing (232). Threaded body (254) includes angular locking body (262) dimensioned to abut against lockout ledge (296) to thereby prevent rotation of threaded body (254) while lockout assembly (290) is in the locked configuration, in accordance with the description herein. Additionally, threaded body (254) defines an input threading (256) and an output threading (258). Input threading (256) extends proximally into a longitudinally extending dwell (260). Input threading (256) is a helically oriented recess, while longitudinally extending dwell (260) is a linear recess located at the proximal end of input threading (256). Input threading (256) and the linear recess of dwell (260) are connected to each other such that a projection may travel between the linear recess of dwell (260) and the helically oriented recess of input threading (256) in an unobstructed fashion.

Input threading (256) and output threading (258) are oriented in opposing angular directions relative to each other such that input threading (256) is oriented in a first angular direction while output threading (258) is oriented in a second, opposite angular direction. In other words, input threading (256) is oriented in a conventional right-hand threaded orientation, while output threading (258) is oriented in a left-hand threaded orientation; or vice versa. Additionally, input threading (256) and output threading (258) may have a different pitch (i.e. grooves per axial length) as compared to each other. For example, input threading (256) may have a larger pitch (more grooves per axial length) as compared to output threading (258). Additionally, the pitch (i.e. grooves per axial length) not be uniform throughout the continuous length of input threading (256) and/or output threading (258). For example, input threading (256) may have a first section with a first pitch (i.e. grooves per axial length), connected to a second section with a second, different pitch (i.e. grooves per axial length), which is in turn connected to a third section with a third, yet still different pitch (i.e. grooves per axial length).

Input projection (282) of second sliding member (280) meshes with input threading (256); while output projection (229) of output drive body (228) meshes with output threading (258). Output projection (229) thus serves as a cam follower in output threading (258). The operator may actuate input projection (282) of second sliding member (280) by actuating knife trigger (251) in accordance with the description herein. For example, the operator may pull knife trigger (251), which in turn actuates first sliding member (272), which in turn actuates second sliding member (280) via transverse driving pin (278) and laterally spaced projection (288). Because input projection (282) meshes with input threading (256), actuation of input projection (282) causes rotation of threaded body (254). Because output projection (229) meshes with output threading (258), rotation of threaded body (254) drives translation of output drive body (228) and knife (220). In other words, translation of input projection (282) within input threading (256) may drive translation of output projection (229) within output threading (258) via rotation of threaded body (254).

Since input threading (256) and output threading (258) are oriented in opposing angular directions relative to each other (i.e. one is threaded left-handed while the other is threaded right-handed), translation of input projection (282) and second sliding member (280) in a first longitudinal direction causes translation of output drive body (228) and knife (220) in a second, opposite, longitudinal direction. For example, the operator may proximally actuate input drive assembly (270) so that input projection (282) cams against input threading (256) to rotate threaded body (254) in a first angular direction. Rotation of threaded body (254) in the first angular direction causes output threading (258) to cam against output projection (229) to drive output drive body (228) and knife (220) in the distal direction. Alternatively, actuation of second sliding member (280) of input drive assembly (270) in the distal direction causes input projection (282) to cam against input threading (256) to rotate threaded body (254) in a second, opposite, angular direction. Rotation of threaded body (254) in the second angular direction causes output threading (258) to cam against output projection (229) to drive output drive body (228) and knife (220) in the proximal direction.

It should be understood that since dwell (260) extends longitudinally along threaded body (254), translation of input projection (282) within dwell (260) does not rotate threaded body (254). Therefore, when second sliding member (280) translates relative to housing (232) such that input projection (282) translates within dwell (260), threaded body (254) does not rotate such that output drive body (228) and knife (220) do not translate relative to housing (232).

If input threading (256) and output threading (258) have different pitches (i.e. grooves per axial length), then the linear distance second sliding member (280) actuates to angularly displace threaded body (254) may be a different than the linear distance knife (220) is driven as a result of threaded body (254) rotating the same angular displacement. In other words, the pitch of input threading (256) and output threading (258) may be different relative to each other such that the translation distance required for second sliding member (280) to drive knife (220) is different than the distance knife (220) is actually driven.

For example, if input threading (256) has a larger pitch (i.e. more grooves per axial length) compared to output threading (258), sliding member (280) will need to translate a shorter distance in order to sufficiently angularly displace threaded body (254) to drive knife (220) from the pre-fired position to the fired position. Therefore, output drive body (228) and knife (220) may translate a greater distance than second sliding member (280) translates to drive output drive body (228) and knife (220). This may effectively shorten the distance knife trigger (251) must translate to drive knife (220) through jaws (212, 214). Similarly, if the grooves per axial length (i.e. pitch) is not be uniform throughout the continuous length of input threading (256) and/or output threading (258), projections (282, 229) will travel different axial distances when traveling along different sections of threading (256, 258), respectively. Therefore, the mechanical advantage of driving knife (220) may be increased or decreased along certain portions of the firing stroke for knife (220).

FIGS. 15A-15F show an exemplary use of lockout assembly (290) and firing assembly (250) in accordance with the teachings herein. Similar to that shown between FIGS. 3A-3B, when the operator desires to initially grasp and manipulate tissue, the operator may pivot resilient arm (234) toward housing (232) to the position shown in FIG. 15A such that jaws (222, 214) are pivoted from the opened position toward the closed position while resilient arm (134) remains in the relaxed position. Therefore, jaws (212, 214) may not provide a sufficient closing force suitable for electrodes (213, 215) to seal tissue grasped by jaws (212, 214). With jaws (212, 214) pivoted toward the closed position, the operator may manipulate tissue grasped by jaws (212, 214). It should be understood that at this moment, knife (220) is in the pre-fired position (similar to knife (120) shown in FIG. 4A).

Additionally, as shown in FIG. 15A, thumb ring (238) does not abut against translating body (292) such that spring (298) biases translating body (292) into the locked position. At this point, if the operator actuated RF trigger (242), electrodes (213, 215) would not activate, as lockout button (245) is still deactivated. Additionally, lockout ledge (296) is directly adjacent to angular locking body (262), thereby preventing rotation of threaded body (254) and actuation of knife (220). Therefore, knife trigger (251) would be prevented from actuating proximally while locking assembly (290) is in the locked configuration, as input projection (282) would not be able to translate within input threading (256) to rotate threaded body (254).

Next, as seen in FIG. 15B, the operator may pivot resilient arm (234) further toward housing (232) such that resilient arm (234) bends to the flexed position. It should be understood that at this point, knife (220) is still in the pre-fired position. However, with resilient arm (234) in the flexed position, thumb ring (238) abuts against translating body (292) to overcome the biasing force provided by spring (298), such that translating body (292) is in the unlocked position. At this point, the closure forces provided by jaws (212, 214) are sufficiently suitable for electrodes (213, 215) to seal tissue grasped by jaws (212, 214). Additionally at this point, lockout button (245) is depressed such that lockout button (245) is activated in accordance with the teachings herein. While translating body (292) is in the unlocked position, lockout ledge (296) no longer interferes with rotation of angular locking body (262) of threaded body (254). Because lockout ledge (296) no longer interferes with the rotation of threaded body (254), firing assembly (250) may actuate knife (220) distally is accordance with the description herein. It should be understood that when the operator no longer presses resilient arm (234) toward housing (232) with enough force to keep arm (234) in the flexed position, the resilient nature of arm (234) will return arm (234) to the relaxed position, allowing spring (298) to bias translating body (292) back into the locked position.

Next, as shown between 15B-15C, when the operator desires to fire knife (220), the operator may pull trigger (251) proximally such that first sliding member (272) and second sliding member (280) move proximally together due to transverse driving pin (288) making contact with projections (288). Therefore, input projection (282) translates proximally within and cams against input threading (256) to rotate threaded body (254) in a first angular direction. Rotation of threaded body (254) in the first angular direction drives cause output threading (258) to cam against output projection (229), thereby translating output drive body (228) and knife (220) distally from the pre-fired position (similar to that shown in FIG. 4A) to the fired position (similar to that shown in FIG. 4B). At the moment shown in FIG. 15C, knife (220) may have actuated substantially through jaws (212, 214), severing tissue captured between jaws (212, 214), similar to the position shown of knife (120) in FIG. 4B.

Because grounding pins (273, 283) are fixed relative to housing (232), movement of sliding bodies (276, 286) compresses biasing members (271, 284) between grounding pins (273, 283) and the interior of sliding bodies (276, 286), such that biasing members (271, 284) impart a distal biasing force on sliding bodies (276, 286), respectively. It should be understood that at the position shown in FIG. 15C, transverse driving pin (278) is just distal to cam surface (233) of slotted pathway (231) such that second bias member (277) is still forces transverse driving pin (278) in the downward position within slot (279). Therefore, transverse driving pin (278) is still in contact with projections (288) such that transverse driving pin (278) overcomes the distal biasing force biasing member (284) imparts on sliding body (286) to drive sliding body (286) back into the pre-fired position (as shown in FIGS. 15A-15B). Additionally, it should be understood that at the position shown in FIG. 15C, input projection (282) is directly adjacent and distal relative to longitudinal dwell (260). Therefore, any further proximal translation of input projection (282) will not rotate threaded body (254), such that any further proximal translation of knife trigger (251) will not distally actuate knife (220).

Figure 15C:
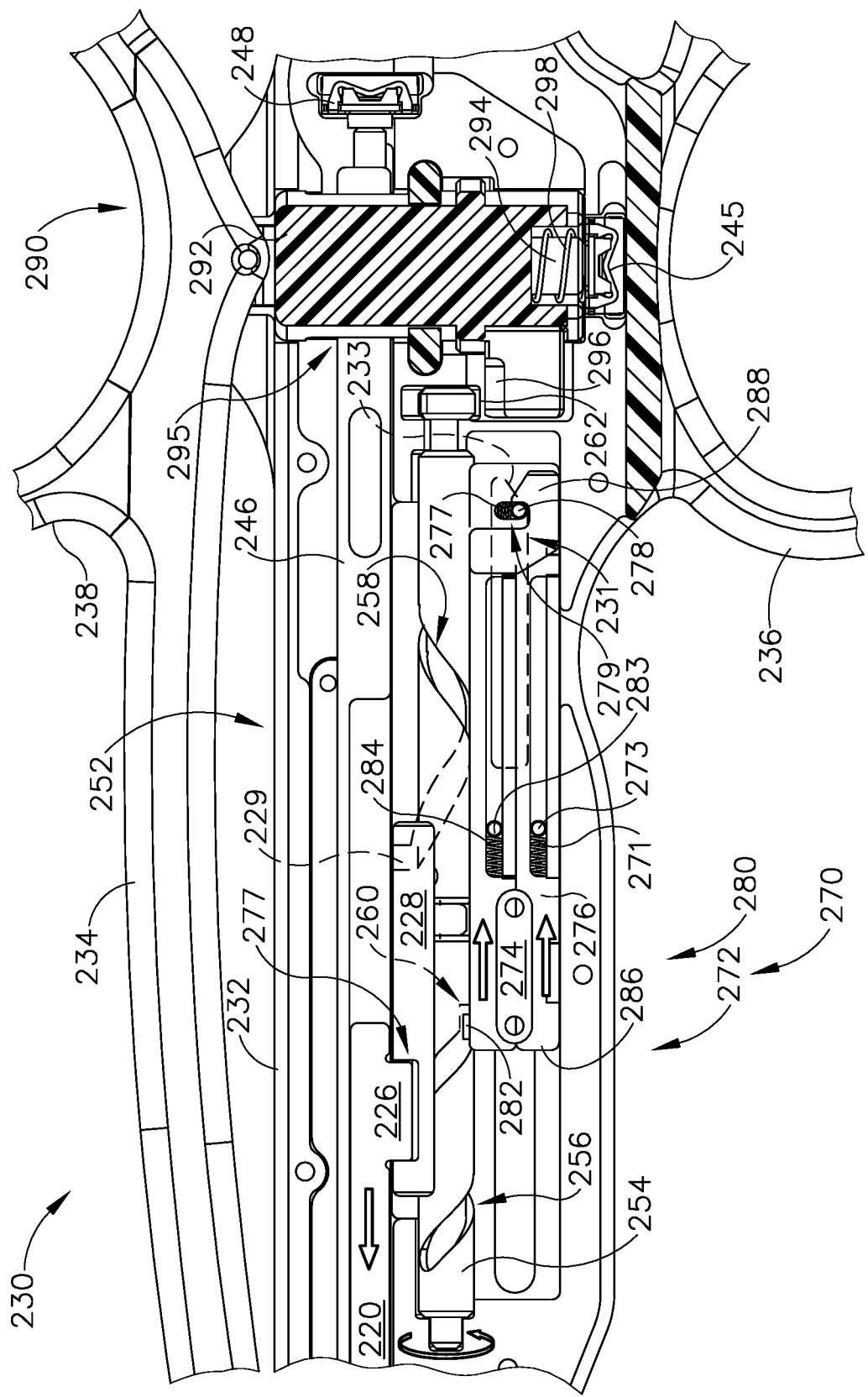
FIG. 15C depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 9 is in the unlocked configuration, and where the firing assembly of FIG. 11 is in a first fired position.
Figure 15D:
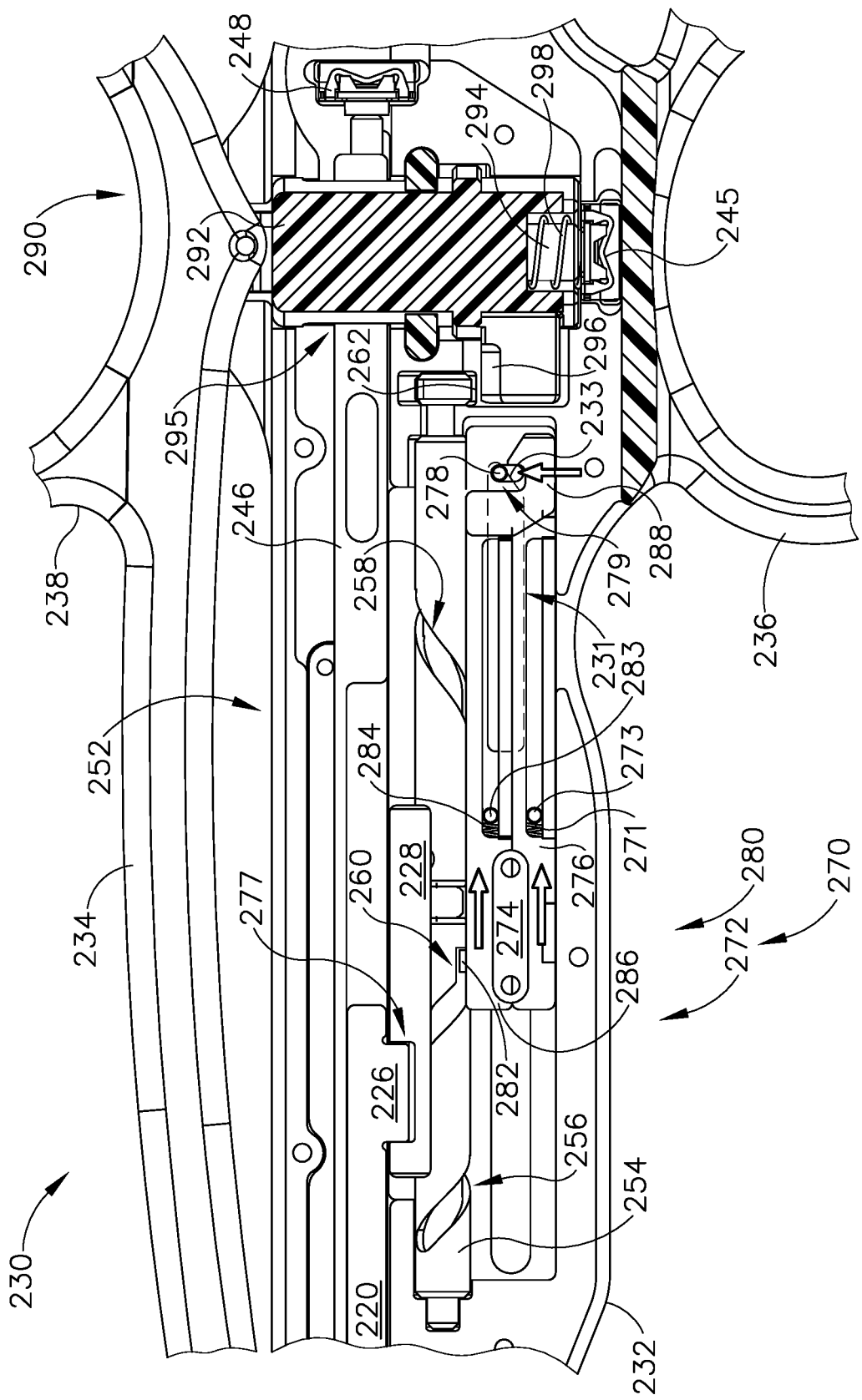
FIG. 15D depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 9 is in the unlocked configuration, and where the firing assembly of FIG. 11 is in a second fired position.
Figure 15E:
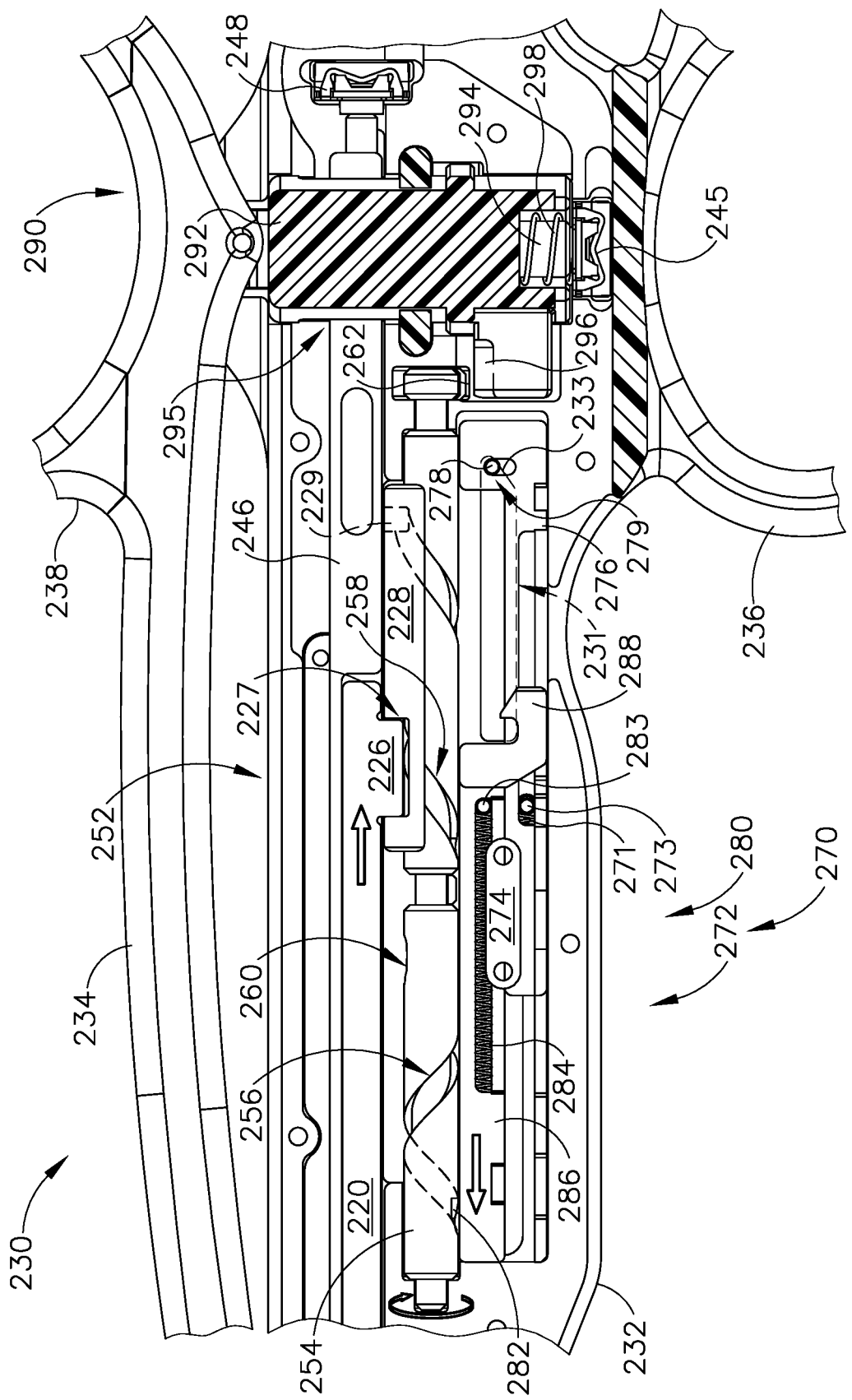
FIG. 15E depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 9 is in the unlocked configuration, and where the firing assembly of FIG. 11 is in a pre-returned, post-fired position.
Figure 15F:
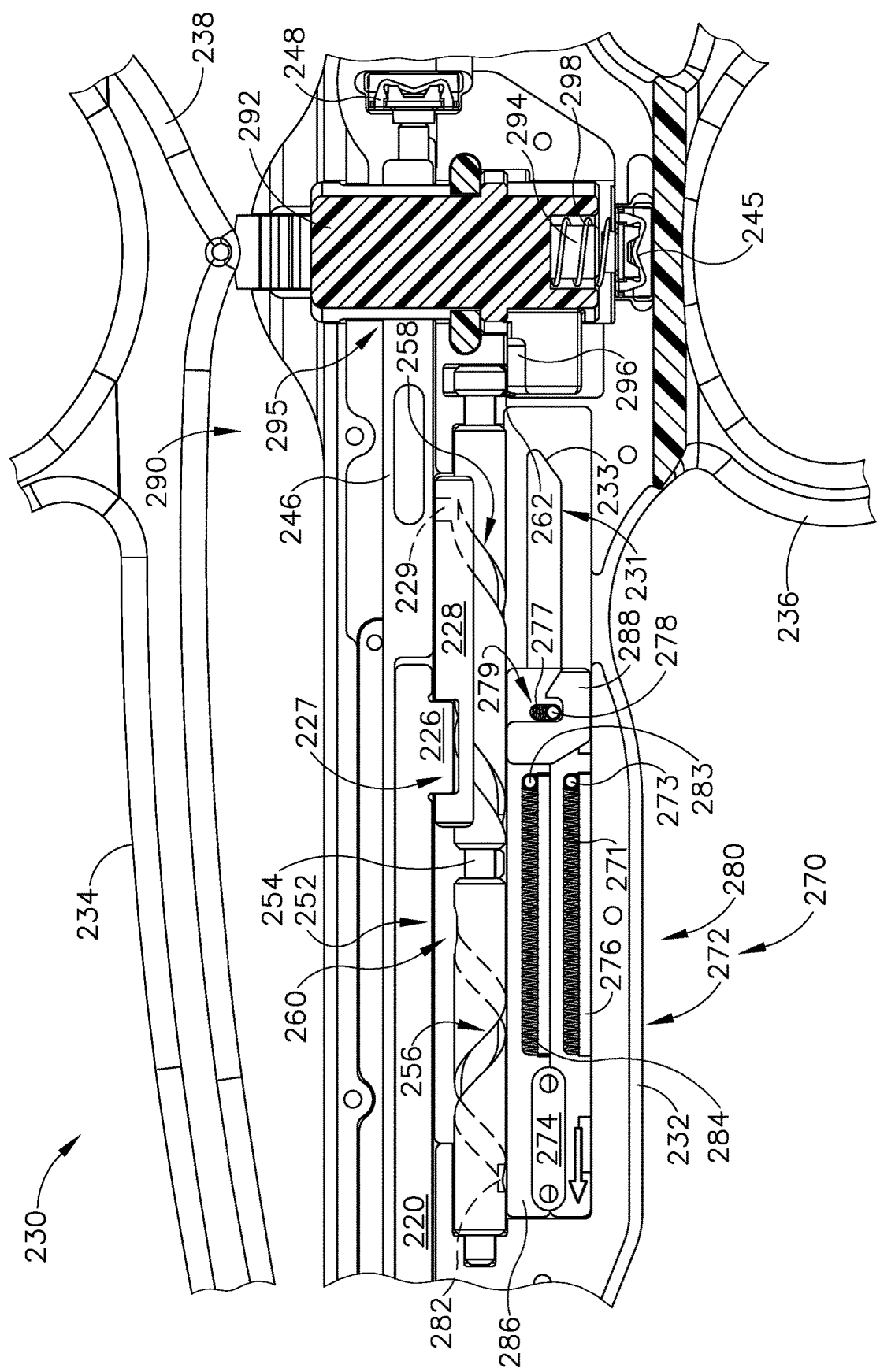
FIG. 15F depicts a side elevational view of a portion of the instrument of FIG. 5, with a portion of the handle assembly of FIG. 7 omitted for clarity, where the end effector is in the closed position, where the resilient arm is in the flexed position, where the lockout assembly of FIG. 9 is in the unlocked configuration, and where the firing assembly of FIG. 11 is returned to the first pre-fired position.

If the operator pulls trigger (251) further in the proximal direction, as shown between FIGS. 15C-15D, transverse driving pin (278) will come into contact with cam surface (233) of slotted pathway (231). It should be understood that since input projection (282) is actuating within dwell (260), threaded body (254) does not rotate. Cam surface (233) pushes transverse driving pin (278) upwards within slot (279), overcoming the biasing force of second biasing member (287). Cam surface (233) may push transverse driving pin (288) upwards until pin (278) is no longer engaged with projections (288), as shown in FIG. 15D. With pin (278) no longer engaged with projections (288), biasing member (284) may push against grounding pin (283), therefore actuating second sliding member (280) in the distal direction, as shown in FIG. 15E. Distal actuation of second sliding member (280) causes threaded body (254) to rotate in the second angular direction, which causes proximal translation of knife (220). In particular, knife (220) may travel all the way back to the pre-fired position. Once actuated proximally past cam surface (233), biasing member (277) may bias transverse pin (278) back within slot (279).

Projections (288) may also interact with transverse driving pin (278) and second biasing member (277) such that projections (288) may push pin (278) upward out of engagement with projections (288) when knife (220) experiences an excess load, such as when knife (220) encounters an undesirable object. For example, if knife (220) encounters an object difficult to cut, projections (288) may overcome the biasing force of second biasing member (277) such that transverse driving pin (278) actuates upward within slot (279). In other words, if knife (220) encounters an object too difficult to cut, contact between projections (288) and transverse driving pin (278) may generate a force the actuates pin (278) within slot (279) such that pin (278) and projection (288) are no longer in engagement, instead of proximally driving second sliding member (280). Therefore, second sliding member (280) decouples with first sliding member (272) prior to knife (220) reaching the fired position, and knife (220) automatically travels back to the pre-fired position due to first biasing member (284) driving sliding body (286) distally. This may help prevent knife (220) from being damaged.

It should be understood that second sliding member (280) returns to the pre-fired position even though first sliding member (272) is still in the fired position. Therefore, once the operator pulls trigger (251) far enough proximally to complete the distal actuation of knife (220), second sliding member (280) may disengage with first sliding member (272) and automatically return knife (220) to the pre-fired position, regardless if the operator holds trigger (251) in the proximal position. In other words, cam surface (233) of slotted pathway (231), transverse pin (288), and biasing members (184, 187) may act as an automatic knife return mechanism to return knife (220) to the pre-fired poison automatically after reaching a predetermined distal location.

As shown between FIGS. 15E-15F, the operator may release trigger (251) such that biasing member (271) pushes first sliding member (272) back to the position shown in FIG. 15A. The operator may then re-fire knife (220) in accordance with the description herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, (ii) an arm associated with the second jaw, wherein the arm is configured to pivot the second jaw between the open position and the closed position; and (c) a knife drive assembly comprising: (i) an input assembly, (ii) an output assembly coupled with the knife, and (iii) a threaded member rotatably disposed within the housing, wherein the threaded member comprises: (A) a first threaded portion associated with the input assembly, wherein the first threaded portion comprises a first pitch extending in a first pitch orientation, and (B) a second threaded portion associated with the output assembly, wherein the second threaded portion comprises a second pitch extending in a second pitch orientation, wherein the second pitch orientation is opposite to the first pitch orientation, wherein the input assembly is configured to travel a first proximal distance to in order to rotate the threaded member, wherein the threaded member is configured to rotate to drive the output assembly a first distal distance to actuate the knife from the pre-fired position toward the fired position.

Example 2

The surgical instrument of Example 1, wherein the input assembly comprises an input projection housed within the first threaded portion, wherein the input projection is configured to drive rotation of the threaded member in response to linear translation of the input projection.

Example 3

The surgical instrument of Example 2, wherein the output assembly comprises an output projection housed within the second threaded portion, wherein the threaded member is configured to drive linear translation of the output projection in response to rotation of the threaded member.

Example 4

The surgical instrument of Example 3, wherein the first threaded portion extends into a longitudinally extending dwell.

Example 5

The surgical instrument of Example 4, wherein the input projection is configured to translate within the longitudinally extending dwell without rotating the threaded member.

Example 6

The surgical instrument of any one or more of Example 1 through 5, wherein the arm comprises a resilient member configured to transition between a relaxed position and a flexed position when the jaws are in the closed configuration.

Example 7

The surgical instrument of Example 6, further comprising a lockout member configured to actuate between a locked configuration and an unlocked configuration.

Example 8

The surgical instrument of Example 7, wherein the lockout arm is configured to drive the lockout member from the locked configuration into the unlocked configuration in response to the arm transitioning from the relaxed position to the flexed position.

Example 9

The surgical instrument of Example 8, wherein the threaded member comprises an angular locking body.

Example 10

The surgical instrument of Example 9, wherein the angular locking body is configured to abut against the lockout member while in the locked configuration to prevent actuation of the knife from the pre-fired position to the fired position.

Example 11

The surgical instrument of any one or more of Examples 1 through 10, wherein the output assembly defines a cutout, wherein the knife further comprises a proximal body housed within the cutout of the output assembly.

Example 12

The surgical instrument of any one or more of Examples 1 through 11, wherein the first distal distance is greater than the first proximal distance.

Example 13

The surgical instrument of any one or more of Examples 1 through 12, wherein the input assembly comprises a first sliding member associated with a trigger and a second sliding member associated with the threaded member, where the second sliding member is distally biased.

Example 14

The surgical instrument of Example 13, wherein the first sliding member is configured to proximally drive the second sliding member to a pre-determined proximal position.

Example 15

The surgical instrument of Example 14, wherein the first sliding member and the second sliding member are configured to be disassociated from each other when the second sliding member reaches the pre-determined proximal position.

Example 16

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, (ii) an arm associated with the second jaw, wherein the arm is pivotably coupled with the housing, wherein the arm is configured to pivot the second jaw between the open configuration and the closed configuration, wherein the arm is configured to transition between a relaxed position and a flexed position while the second jaw is in the closed configuration; and (c) a knife drive assembly comprising: (i) an input assembly, (ii) an output assembly coupled with the knife, and (iii) a threaded member rotatably disposed within the housing, wherein the threaded member comprises: (A) a first threaded portion associated with the input assembly, wherein the first threaded portion extends in a first helical orientation, and (B) a second threaded portion associated with the output assembly, wherein the second threaded portion extends in a second helical orientation, wherein the second helical orientation is opposite to the first helical orientation, wherein the input assembly is configured to travel a first proximal distance to in order to rotate the threaded member, wherein the threaded member is configured to configured rotate to drive the output assembly a first distal distance to actuate the knife from the pre-fired position toward the fired position.

Example 17

The surgical instrument of Example 16, wherein the arm further comprises a resilient member configured to transition between a relaxed position and a flexed position while the second jaw is in the closed configuration.

Example 18

The surgical instrument of Example 17, further comprising a lockout assembly configured to transition between an unlocked position and a locked position in response to the resilient arm transition between the relaxed position and the flexed position.

Example 19

A surgical instrument comprising: (a) a housing extending distally into a first jaw; (b) an arm pivotably coupled with the housing, wherein the arm extends distally into a second jaw, wherein arm is operable to drive the second jaw between an open position and a closed position; (c) an electrode assembly associated with the first jaw and the second jaw, wherein the electrode assembly is configured to apply RF energy to tissue; (d) a knife configured to actuate within the first jaw and the second jaw between a pre-fired position and a fired position; (e) a trigger assembly movably coupled with the housing, and (f) a knife actuation assembly configured to actuate the knife between the pre-fired position and the fired position, wherein the knife actuation assembly comprises: (i) a threaded body rotatably disposed within the housing, wherein the threaded body defines an input threading, and an output threading, (ii) an output member slidably coupled with the threaded body, wherein the output member comprises an output projection housed within the output threading, and (iii) an input member slidably coupled with the threaded body, wherein the input member comprises an input projection associated with the input threading, wherein the trigger assembly is configured to drive the input projection between a first position, and a second position relative to the threaded body, wherein the input projection is housed within the input threading between the first position and the second position such that the knife actuation assembly is configured to drive the knife between the pre-fired position and the fired position.

Example 20

The surgical instrument of Example 19, wherein the threaded body further defines a longitudinal dwell extending into the input threading, wherein the trigger is configured to drive the input projection between the second position and a third position relative to the threaded body, wherein the input projection is housed within the longitudinal dwell between the second position and the third position such that the knife actuation assembly does not drive the knife in response to movement of the trigger assembly, wherein the input member is configured to decouple from the trigger assembly upon reaching the third position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. App. No. 15/989,424, entitled "Method and Apparatus for Open Electrosurgical Shears," filed on May 25, 2018, published as U.S. Pub. No. 2019/0357962 on Nov. 28, 2019; U.S. App. Ser. No. 15/989,430, entitled "Electrosurgical Shears with Knife Lock and Clamp-Actuated Switch," filed on May 25, 2018, published as U.S. Pub. No. 2019/0357969 on Nov. 28, 2019; U.S. App. Ser. No. 15/989,433, entitled "Knife Drive Assembly for Electrosurgical Shears," filed May 25, 2018, published as U.S. Pub. No. 2019/0357963 on Nov. 28, 2019; U.S. App. No. 15/989,438, entitled "Knife Auto-Return Assembly for Electrosurgical Shears," filed on May 25, 2018, published as U.S. Pub. No. 2019/0357964 on Nov. 28, 2019; U.S. App. Ser. No. 15/989,448, entitled "Firing and Lockout Assembly for Knife for Electrosurgical Shears," filed on May 25,2018, published as U.S. Pub. No. 2019/0357966 on Nov. 28, 2019; U.S. App. Ser. No. 15/989,452, entitled "Dual Stage Energy Activation for Electrosurgical Shears," filed on May 25, 2018, published as U.S. Pub. No. 2019/0357967 on Nov. 28, 2019; and U.S. App. Ser. No. 15/989,455, entitled "Latching Clamp Arm for Electrosurgical Shears," filed on May 25, 2018, published as U.S. Pub. No. 2019/0357968 on Nov. 28, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument comprising:
   (a) an end effector, wherein the end effector comprises:
      (i) a first jaw,
      (ii) a second jaw pivotably coupled with the first jaw, wherein the second jaw is operable to move between an open position and a closed position,
      (iii) a knife configured to actuate between a pre-fired position and a fired position, and
      (iv) an electrode assembly configured to apply RF energy to tissue;
   (b) a handle assembly, wherein the handle assembly comprises:
      (i) a housing associated with the first jaw,
      (ii) an arm associated with the second jaw, wherein the arm is configured to pivot the second jaw between the open position and the closed position; and
   (c) a knife drive assembly comprising:
      (i) an input assembly,
      (ii) an output assembly coupled with the knife, and
      (iii) a threaded member rotatably disposed within the housing, wherein the threaded member comprises:
         (A) a first threaded portion associated with the input assembly, wherein the first threaded portion comprises a first pitch extending in a first pitch orientation, and
         (B) a second threaded portion associated with the output assembly, wherein the second threaded portion comprises a second pitch extending in a second pitch orientation, wherein the second pitch orientation is opposite to the first pitch orientation,
      wherein the input assembly is configured to travel a first proximal distance to in order to rotate the threaded member, wherein the threaded member is configured to rotate to drive the output assembly a first distal distance to actuate the knife from the pre-fired position toward the fired position.

2. The surgical instrument of claim 1, wherein the input assembly comprises an input projection housed within the first threaded portion, wherein the input projection is configured to drive rotation of the threaded member in response to linear translation of the input projection.

3. The surgical instrument of claim 2, wherein the output assembly comprises an output projection housed within the second threaded portion, wherein the threaded member is configured to drive linear translation of the output projection in response to rotation of the threaded member.

4. The surgical instrument of claim 3, wherein the first threaded portion extends into a longitudinally extending dwell.

5. The surgical instrument of claim 4, wherein the input projection is configured to translate within the longitudinally extending dwell without rotating the threaded member.

6. The surgical instrument of claim 1, wherein the arm comprises a resilient member configured to transition between a relaxed position and a flexed position when the jaws are in the closed configuration.

7. The surgical instrument of claim 6, further comprising a lockout member configured to actuate between a locked configuration and an unlocked configuration.

8. The surgical instrument of claim 7, wherein the lockout arm is configured to drive the lockout member from the locked configuration into the unlocked configuration in response to the arm transitioning from the relaxed position to the flexed position.

9. The surgical instrument of claim 8, wherein the threaded member comprises an angular locking body.

10. The surgical instrument of claim 9, wherein the angular locking body is configured to abut against the lockout member while in the locked configuration to prevent actuation of the knife from the pre-fired position to the fired position.

11. The surgical instrument of claim 1, wherein the output assembly defines a cutout, wherein the knife further comprises a proximal body housed within the cutout of the output assembly.

12. The surgical instrument of claim 1, wherein the first distal distance is greater than the first proximal distance.

13. The surgical instrument of claim 1, wherein the input assembly comprises a first sliding member associated with a trigger and a second sliding member associated with the threaded member, where the second sliding member is distally biased.

14. The surgical instrument of claim 13, wherein the first sliding member is configured to proximally drive the second sliding member to a pre-determined proximal position.

15. The surgical instrument of claim 14, wherein the first sliding member and the second sliding member are configured to be disassociated from each other when the second sliding member reaches the pre-determined proximal position.

16. A surgical instrument comprising:
   (a) an end effector, wherein the end effector comprises:
      (i) a first jaw,
      (ii) a second jaw pivotably coupled with the first jaw, wherein the second jaw is operable to move between an open position and a closed position,
      (iii) a knife configured to actuate between a pre-fired position and a fired position, and
      (iv) an electrode assembly configured to apply RF energy to tissue;
   (b) a handle assembly, wherein the handle assembly comprises:
      (i) a housing associated with the first jaw,
      (ii) an arm associated with the second jaw, wherein the arm is pivotably coupled with the housing, wherein the arm is configured to pivot the second jaw between the open configuration and the closed configuration, wherein the arm is configured to transition between a relaxed position and a flexed position while the second jaw is in the closed configuration; and
   (c) a knife drive assembly comprising:
      (i) an input assembly,
      (ii) an output assembly coupled with the knife, and
      (iii) a threaded member rotatably disposed within the housing, wherein the threaded member comprises:
         (A) a first threaded portion associated with the input assembly, wherein the first threaded portion extends in a first helical orientation, and
         (B) a second threaded portion associated with the output assembly, wherein the second threaded portion extends in a second helical orientation, wherein the second helical orientation is opposite to the first helical orientation, wherein the input assembly is configured to travel a first proximal distance to in order to rotate the threaded member, wherein the threaded member is configured to configured rotate to drive the output assembly a first distal distance to actuate the knife from the pre-fired position toward the fired position.

17. The surgical instrument of claim 16, wherein the arm further comprises a resilient member configured to transition between a relaxed position and a flexed position while the second jaw is in the closed configuration.

18. The surgical instrument of claim 17, further comprising a lockout assembly configured to transition between an unlocked position and a locked position in response to the resilient arm transition between the relaxed position and the flexed position.

19. A surgical instrument comprising:
(a) a housing extending distally into a first jaw;
(b) an arm pivotably coupled with the housing, wherein the arm extends distally into a second jaw, wherein arm is operable to drive the second jaw between an open position and a closed position;
(c) an electrode assembly associated with the first jaw and the second jaw, wherein the electrode assembly is configured to apply RF energy to tissue;
(d) a knife configured to actuate within the first jaw and the second jaw between a pre-fired position and a fired position;
(e) a trigger assembly movably coupled with the housing, and
(f) a knife actuation assembly configured to actuate the knife between the pre-fired position and the fired position, wherein the knife actuation assembly comprises:
    (i) a threaded body rotatably disposed within the housing, wherein the threaded body defines an input threading, and an output threading,
    (ii) an output member slidably coupled with the threaded body, wherein the output member comprises an output projection housed within the output threading, and
    (iii) an input member slidably coupled with the threaded body, wherein the input member comprises an input projection associated with the input threading, wherein the trigger assembly is configured to drive the input projection between a first position, and a second position relative to the threaded body, wherein the input projection is housed within the input threading between the first position and the second position such that the knife actuation assembly is configured to drive the knife between the pre-fired position and the fired position.

20. The surgical instrument of claim 19, wherein the threaded body further defines a longitudinal dwell extending into the input threading, wherein the trigger is configured to drive the input projection between the second position and a third position relative to the threaded body, wherein the input projection is housed within the longitudinal dwell between the second position and the third position such that the knife actuation assembly does not drive the knife in response to movement of the trigger assembly, wherein the input member is configured to decouple from the trigger assembly upon reaching the third position.

* * * * *